United States Patent
Shouldice et al.

(10) Patent No.: US 12,033,485 B2
(45) Date of Patent: *Jul. 9, 2024

(54) APPARATUS, SYSTEM, AND METHOD FOR MOTION SENSING

(71) Applicant: ResMed Sensor Technologies Limited, Sandyford (IE)

(72) Inventors: Redmond Shouldice, Sandyford (IE); Stephen McMahon, Sandyford (IE); Michael Wren, Sandyford (IE)

(73) Assignee: ResMed Sensor Technologies Limited (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/177,889

(22) Filed: Mar. 3, 2023

(65) Prior Publication Data
US 2024/0005768 A1 Jan. 4, 2024

Related U.S. Application Data

(63) Continuation of application No. 15/733,162, filed as application No. PCT/EP2018/086764 on Dec. 21, 2018, now Pat. No. 11,615,688.

(Continued)

(51) Int. Cl.
*G08B 21/04* (2006.01)
*G06F 21/32* (2013.01)
(Continued)

(52) U.S. Cl.
CPC ......... *G08B 21/0469* (2013.01); *G06F 21/32* (2013.01); *G08B 5/222* (2013.01);
(Continued)

(58) Field of Classification Search
CPC ....... A61B 5/113; A61B 5/024; A61B 5/7228; A61B 5/1113; A61B 5/0816; A61B 5/1135; A61B 5/08
See application file for complete search history.

(56) References Cited

U.S. PATENT DOCUMENTS

| 6,661,345 B1 | 12/2003 | Bevan et al. |
| RE42,471 E | 6/2011 | Torch |

(Continued)

FOREIGN PATENT DOCUMENTS

| CN | 101917903 A | 12/2010 |
| CN | 204306833 U | 5/2015 |

(Continued)

OTHER PUBLICATIONS

Examination Report issued in corresponding EP application No. 18833058.3 on Jan. 4, 2022.

(Continued)

*Primary Examiner* — Mirza F Alam
(74) *Attorney, Agent, or Firm* — Botos Churchill IP Law LLP

(57) ABSTRACT

Methods and devices provide physiological movement detection, such as gesture, breathing, cardiac and/or gross body motion, with active sound generation such as for an interactive audio device. The processor may evaluate, via a microphone coupled to the interactive audio device, a sensed audible verbal communication. The processor may control producing, via a speaker coupled to the processor, a sound signal in a user's vicinity. The processor may control sensing, via a microphone coupled to the processor, a reflected sound signal. This reflected sound signal is a reflection of the generated sound signal from the vicinity or user. The processor may process the reflected sound, such as by a demodulation technique, to derive a physiological movement signal. The processor may generate, in response to the sensed audible verbal communication, an output based on an evaluation of the derived physiological movement signal.

31 Claims, 9 Drawing Sheets

Related U.S. Application Data

(60) Provisional application No. 62/610,013, filed on Dec. 22, 2017.

(51) Int. Cl.

| | | |
|---|---|---|
| *G08B 5/22* | (2006.01) | |
| *G08B 21/06* | (2006.01) | |
| *G08B 21/22* | (2006.01) | |
| *G08B 27/00* | (2006.01) | |
| *G10L 25/51* | (2013.01) | |
| *G10L 25/78* | (2013.01) | |

(52) U.S. Cl.
CPC ......... *G08B 21/0423* (2013.01); *G08B 21/06* (2013.01); *G08B 21/22* (2013.01); *G08B 27/005* (2013.01); *G10L 25/51* (2013.01); *G10L 25/78* (2013.01)

(56) References Cited

U.S. PATENT DOCUMENTS

| | | |
|---|---|---|
| 8,562,526 B2 | 10/2013 | Heneghan et al. |
| 8,841,994 B2 | 9/2014 | Li |
| 8,874,301 B1 | 10/2014 | Rao et al. |
| 9,430,938 B2 | 8/2016 | Proud |
| 9,489,817 B2 | 11/2016 | Gui |
| 9,500,489 B1 | 11/2016 | Ng |
| 9,862,271 B2 | 1/2018 | Brankovic et al. |
| 9,883,821 B2 | 2/2018 | Muehlsteff |
| 9,993,166 B1 | 6/2018 | Johnson et al. |
| 10,004,451 B1 | 6/2018 | Proud |
| 10,004,873 B1 | 6/2018 | Hur et al. |
| 10,009,581 B2 | 6/2018 | Proud |
| 10,159,421 B2 | 12/2018 | Heneghan |
| 2004/0039254 A1 | 2/2004 | Stivoric et al. |
| 2005/0073424 A1 | 4/2005 | Ruoss et al. |
| 2008/0077015 A1 | 3/2008 | Boric-Lubecke et al. |
| 2008/0183388 A1 | 7/2008 | Goodrich |
| 2010/0240945 A1* | 9/2010 | Bikko ............... A61B 5/486 600/28 |
| 2011/0068935 A1 | 3/2011 | Riley et al. |
| 2012/0150387 A1* | 6/2012 | Watson ............ A61B 5/0077 701/1 |
| 2013/0172770 A1 | 7/2013 | Muehlsteff |
| 2013/0231579 A1 | 9/2013 | Shigeto |
| 2013/0345921 A1 | 12/2013 | Al-Ali et al. |
| 2014/0163343 A1 | 6/2014 | Heneghan et al. |
| 2014/0276165 A1* | 9/2014 | Addison ............ A61B 7/003 600/529 |
| 2015/0193193 A1 | 7/2015 | Khaira et al. |
| 2015/0223731 A1* | 8/2015 | Sahin .............. A61B 5/16 600/595 |
| 2016/0357185 A1 | 12/2016 | Laur et al. |
| 2017/0143253 A1 | 5/2017 | Krenzer et al. |
| 2017/0180911 A1 | 6/2017 | Burton |
| 2017/0212235 A1 | 7/2017 | Qiu et al. |
| 2017/0232915 A1 | 8/2017 | Dufford |
| 2017/0341658 A1 | 11/2017 | Fung et al. |
| 2017/0347951 A1* | 12/2017 | Gollakota .......... A61B 5/1126 |
| 2018/0022358 A1 | 1/2018 | Fung et al. |
| 2018/0203451 A1 | 7/2018 | Cronin et al. |
| 2018/0287651 A1 | 10/2018 | Fernando et al. |
| 2018/0290020 A1* | 10/2018 | Vissa ............... H04L 67/52 |
| 2019/0133511 A1 | 5/2019 | Migneco et al. |
| 2020/0365275 A1 | 11/2020 | Barnett et al. |
| 2021/0150873 A1 | 5/2021 | Shouldice et al. |

FOREIGN PATENT DOCUMENTS

| | | |
|---|---|---|
| CN | 106456000 A | 2/2017 |
| CN | 106913339 A | 7/2017 |
| CN | 107405081 A | 11/2017 |
| CN | 108113706 A | 6/2018 |
| DE | 10259522 A1 | 7/2004 |
| DE | 102008038022 A1 | 3/2009 |
| DE | 102015122245 A1 | 6/2017 |
| EP | 1308812 A2 | 5/2003 |
| EP | 2637385 A2 | 9/2013 |
| EP | 2638855 A1 | 9/2013 |
| FR | 3028741 A1 | 5/2016 |
| JP | 2005537721 A | 12/2005 |
| JP | 2006510880 A | 3/2006 |
| JP | 2010012018 A | 1/2010 |
| JP | 2012239748 A | 12/2012 |
| JP | 2014138661 A | 7/2014 |
| JP | 2016107095 A | 6/2016 |
| JP | 2016532481 A | 10/2016 |
| JP | 2016193020 A | 11/2016 |
| JP | 2017064338 A | 4/2017 |
| KR | 20150072821 A | 6/2015 |
| KR | 20170015214 A | 2/2017 |
| WO | 2004021134 A2 | 3/2004 |
| WO | 2004100100 A1 | 11/2004 |
| WO | 2008057883 A2 | 5/2008 |
| WO | 2007143535 A3 | 8/2008 |
| WO | 2010036700 A1 | 4/2010 |
| WO | 2010091168 A1 | 8/2010 |
| WO | 2013177621 A1 | 12/2013 |
| WO | 2014015238 A1 | 1/2014 |
| WO | 2014047310 A1 | 3/2014 |
| WO | 2015006364 A2 | 1/2015 |
| WO | 2015041892 A1 | 3/2015 |
| WO | 2015054134 A1 | 4/2015 |
| WO | 2015061848 A1 | 5/2015 |
| WO | 2015179911 A1 | 12/2015 |
| WO | 2016021235 A1 | 2/2016 |
| WO | 2016093927 A2 | 6/2016 |
| WO | 2016145483 A1 | 9/2016 |
| WO | 2016170005 A1 | 10/2016 |
| WO | 2016170011 A1 | 10/2016 |
| WO | 2016188826 A1 | 12/2016 |
| WO | 2017024085 A1 | 2/2017 |
| WO | 2017029284 A1 | 2/2017 |
| WO | 2017029317 A1 | 2/2017 |
| WO | 2017032873 A2 | 3/2017 |
| WO | 2017032873 A3 | 4/2017 |
| WO | 2017097907 A1 | 6/2017 |
| WO | 2017098609 A1 | 6/2017 |
| WO | 2017100605 A1 | 6/2017 |
| WO | 2017102614 A1 | 6/2017 |
| WO | 2017167731 A1 | 10/2017 |
| WO | 2018033574 A1 | 2/2018 |
| WO | 2018050913 A1 | 3/2018 |

OTHER PUBLICATIONS

Examination Report issued in corresponding EP application No. 18833244.9 on Jan. 3, 2022.
Final OA mailed Mar. 8, 2022 for U.S. Appl. No. 15/733,162.
Non Final Office Action mailed Sep. 21, 2021 for U.S. Appl. No. 15/733,162.
Notice of Allowance issued in Japanese Patent Application No. 2020-534829, mailed Nov. 25, 2022, 3 pages.
Office Action for corresponding EP Application No. 18833058.3-1113 dated Jul. 15, 2022.
Office Action for corresponding European Patent Application No. 18833244.9-1126, dated Jul. 1, 2022.
Office Action issued in corresponding Japanese Patent Application No. 2020-534898, mailed Nov. 22, 2022, 12 pages.
Office Action issued in corresponding Japanese Patent Application No. 2020-534935, mailed Nov. 22, 2022, 17 pages.
Partial International Search Report issued on Mar. 25, 2019.
PCT International Search Report issued in corresponding PCT application No. PCT/EP2018/086764 on May 29, 2019.
Restriction Requirement Office Action dated Jun. 14, 2021 for U.S. Appl. No. 15/733,162.
"Sleep as Android", https://sleep.urbandroid.org/https://sleep.urbandroid.org/documentation/.
"SleepScore", https://www.medgadget.com/2017/11/sleepscore-labs-releases-contact-free-sleep-monitoring-system.html https://www.sleepscore.com/sleepscore-high-low/, Nov. 15, 2017.

(56) References Cited

OTHER PUBLICATIONS

Condliffe, Jamie, "This App Lets You Control Your Phone Using Sonar", https://www.technologyreview.com/s/602834/this-app-lets-you-control-your-phone-using-sonar/, Nov. 15, 2016.
Nandakumar, Rajalakshmi, et al., "Contactless Sleep Apnea Detection on Smartphones", May 18, 2015.
Sangeetha, M., et al., "Embedded ECG Based Real Time Monitoring and Control of Driver Drowsiness Condition", http://article.sciencepublishinggroup.com/html/10.11648.j.ijsts.20150304.17.html, Jul. 2015.
Shin, Heung-Sub, "Real Time Car Driver's Condition Monitoring System", http://web.ee.nchu.edu.tw/~ljh/paper/Real Time Car Driver's Condition Monitoring System.pdf, Jul. 2010.
Wang, Xuyu, et al., "SonarBeat: Sonar Phase for Breathing Beat Monitoring with Smartphones", Department of Electrical and Computer Engineering, Auburn University, Auburn, AL 36849-5201, USA, Aug. 3, 2017.
First Office Action issued in corresponding Chinese Patent Application No. 201880087490.X, mailed Dec. 5, 2022, 30 pages.
Office Action from corresponding CN Application No. 201880087497.1 dated Jan. 18, 2023, 11 pages.
Office Action issued in corresponding Korean Patent Application No. 10-2020-7021037, mailed Feb. 28, 2023, 22 pages.
Office Action issued in corresponding Japanese Patent Application No. 2020-534935, mailed Sep. 1, 2023, 10 pages.

\* cited by examiner

APPARATUS, SYSTEM, AND METHOD FOR MOTION SENSING

1 CROSS REFERENCE TO RELATED APPLICATIONS

This application is a continuation of U.S. patent application Ser. No. 15/733,162, filed on Jun. 2, 2020, which is a national phase entry under 35 U.S.C. § 371 of International Application No. PCT/EP2018/086764 filed Dec. 21, 2018, published in English, which claims the benefit of U.S. Provisional Patent Application No. 62/610,013, filed Dec. 22, 2017, the disclosures of all of which are incorporated herein by reference.

2 BACKGROUND OF THE TECHNOLOGY

2.1 Field of the Technology

The present technology relates to detecting bio-motion associated with living subjects with audio equipment. More particularly, the present technology relates to using acoustic sensing with audio equipment to detect physiological characteristics such as physiological movement such as breathing movement, cardiac movement and/or other less cyclical body movement of a living subject.

2.2 Description of the Related Art

Monitoring the breathing and body (including limb) movement of a person, for example, during sleep, can be useful in many ways. For example, such monitoring could be useful in monitoring and/or diagnosing sleep disordered breathing conditions, such as sleep apnea. Traditionally, the barrier to entry for active radio location or ranging application is that specialized hardware circuitry and antennas are required.

Smartphones and other portable and inconspicuous processing or electronic communication devices have been ubiquitous in daily life, even in developing countries where landlines are not available. For example, many homes contain audio devices that are capable of emitting and recording sounds—e.g., smart speakers, active sound bars, smart devices, smart TVs, and other devices. Such devices may support voice commands using virtual assistants that process received verbal commands and respond with audio output.

It would be desirable to have methods for monitoring bio-motion (i.e., physiological movement) in an efficient, effective manner. The realization of such a system and method would address a considerable technical challenge.

3 BRIEF SUMMARY OF THE TECHNOLOGY

The present technology concerns systems, methods, and apparatus for detecting movement of a subject, for example, while the subject is asleep. Based on such movement detection, including for example breathing movement, the subject's movements, sleep related characteristics, respiratory characteristics, cardiac characteristics, sleep state, etc. may be detected. More particularly, an application associated with processor-enabled audio equipment, such as an interactive audio device or other processing device, such as a smartphone, tablet, smart speaker etc. applies audio functions of the processing device sensors, such as an integrated, and/or externally connectable, speaker(s) and microphone(s) to detect motion. The term "device" herein is used in a broad sense and may include a system, centralized or distributed, that may include one or more speakers, one or more microphones and one or more processors. However, in some versions it may also be an integrated device such as to substantially provide the components and any one or more of the features of the sensing/detection methodologies described herein as a unit. For example, the processing device with its methodologies and sensing components may be integrated in a unitary housing, such as a hand-held system (e.g., sensing configured smart phone) or other such portable system.

Some versions of the present technology may include a processor-readable medium, having stored thereon processor-executable instructions which, when executed by a processor, cause the processor to detect physiological parameters such as with detection of physiological movement of a user. Physiological movement may include any one or more of respiration movement, cardiac movement, limb movement, gesture movement and gross body movement. Physiological parameters may also include one or more characteristics derived from the detected physiological movement (e.g., respiratory amplitude, relative respiratory amplitude, respiratory rate, respiratory rate variability, cardiac amplitude, relative cardiac amplitude, cardiac rate, cardiac rate variability etc.), as well as other characteristics (e.g., (a) presence state (present absent); (b) sleep state, such as, awake or sleep; (c) sleep stage such as N-REM 1 (non-REM light sleep sub-stage 1), N-REM 2 (non-REM light sleep sub-stage 2), N-REM 3 (non-REM deep sleep (also referred to as slow wave sleep (SWS))), REM sleep etc.; or other sleep-related parameters such as (d) fatigue and/or (e) sleepiness; etc.) that may be derived from other physiological parameters. The processor-executable instructions may comprise instructions to control producing, via a speaker coupled to an interactive audio device, a sound signal in a vicinity that may include a user. The processor-executable instructions may comprise instructions to control sensing, via a microphone coupled to the interactive audio processing device, a sound signal reflected from the user. The processor-executable instructions may comprise instructions to process the sensed sound signal. The processor-executable instructions may comprise instructions to evaluate, via the microphone coupled to the interactive audio device, a sensed audible verbal communication. The processor-executable instructions may comprise instructions to derive a physiological movement signal with the sound signal and the reflected sound signal. The processor-executable instructions may comprise instructions to generate, in response to the sensed audible verbal communication, an output based on an evaluation of the derived physiological movement signal.

Some versions of the present technology include a processor-readable medium, having stored thereon processor-executable instructions which, when executed by a processor of an interactive audio device, cause the processor to detect physiological movement of a user. The processor-executable instructions may include instructions to control producing, via a speaker coupled to the interactive audio device, a sound signal in a vicinity of the interactive audio device. The processor-executable instructions may include instructions to control sensing, via a microphone coupled to the interactive audio device, a reflected sound signal from the vicinity. The processor-executable instructions may include instructions to derive a physiological movement signal with at least a portion of the sensed reflected sound signal and a signal representative of at least a portion of the sound signal. The processor-executable instructions may include instructions to generate an output based on an evaluation of at least a portion of the derived physiological movement signal.

In some versions, at least a portion of the produced sound signal, such as the portion used for sensing, may be in a substantially inaudible sound range. At least the portion of the produced sound signal may be a low frequency ultrasonic acoustic signal. The signal representative of the portion of the sound signal may comprise an internally generated oscillator signal or a direct path measured signal. The instructions to derive the physiological movement signal may be configured to derive the physiological movement signal (a) with at least a portion of the produced sound signal and at least portion of the sensed reflected sound signal or (b) with the portion of the sensed reflected sound signal and an associated signal that may be associated with at least a portion of the produced sound signal. Optionally the associated signal may be an internally generated oscillator signal or a direct path measured signal. The instructions to derive the physiological movement signal may be configured to multiply an oscillator signal with the portion of the sensed reflected sound signal. The derived physiological movement signal may include one or more of respiratory motion, gross motion, or cardiac motion or a detection of any one or more of such motion. The medium may further may include processor-executable instructions to evaluate, via the microphone coupled to the interactive audio device, a sensed audible verbal communication; and wherein the instructions to generate the output may be configured to generate the output in response to the sensed audible verbal communication. The processor-executable instructions to derive the physiological movement signal comprise demodulation of the portion of the sensed reflected sound signal with at least a portion of the sound signal. The demodulation may include a multiplication of the portion of the sound signal and the portion of the sensed reflected sound signal.

The processor-executable instructions to control producing the sound signal may generate a dual tone frequency modulated continuous wave signal. The dual tone frequency modulated continuous wave signal may comprise a first sawtooth frequency change overlapped with a second sawtooth frequency change in a repeated waveform. The medium may include processor-executable instructions to generate an ultra-wide band (UWB) sound signal as audible white noise, and wherein the processor-readable medium may include instructions to detect user motion with the UWB sound signal. The medium may further may include processor-executable instructions to generate, in a setup process, probing acoustic sequences from the speaker to calibrate distance measurement of low frequency ultrasonic echoes. The medium may include processor-executable instructions to generate, in a setup process, time synchronized calibration acoustic signals from one or more speakers, including the speaker, to estimate a distance between the microphone and another microphone of the interactive audio device. The medium may include processor-executable instructions to operate a beam forming process to further localize a detected area. The generated output based on the evaluation of the derived physiological movement signal may include monitored user sleep information.

In some versions, the evaluation of the portion of the derived physiological movement signal may include detecting one or more physiological parameters. The one or more physiological parameters may include any one or more of breathing rate, relative amplitude of breathing, cardiac amplitude, relative cardiac amplitude, heart rate and heart rate variability. The monitored user sleep information may include any of a sleep score, a sleep stage and a time in a sleep stage. The generated output may include an interactive query and response presentation. The generated interactive query and response presentation may be effected by way of a speaker. The generated interactive query and response presentation may include advice to improve monitored user sleep information. The generated output based on the evaluation of the portion of the derived physiological movement signal may be further based on accessing a server on a network and/or conducting a search of a network resource. The search may be based on historic user data. The generated output based on the evaluation of at least a portion of the derived physiological movement signal may include a control signal to control an automated appliance or a system. The medium may further include processor control instructions to transmit the control signal to the automated appliance or system over a network. The network may be an internet.

Optionally, the medium may further include processor control instructions to generate a control signal to change a setting of the interactive audio device based on an evaluation of at least a portion of the derived physiological movement signal. The control signal to change a setting of the interactive audio device may include a change in volume based on a detection of user distance from the interactive audio device, user's state or user's location. The processor-executable instructions may be configured to evaluate motion characteristics of different acoustic sensing ranges to monitor sleep characteristics of a plurality of users. The instructions to control producing the sound signal, may control producing simultaneous sensing signals at different sensing frequencies for sensing different users with different frequencies. The instructions to control producing the sound signal, may control producing interleaved acoustic sensing signals for sensing different users at different times. The medium may further include processor-executable instructions to detect presence or absence of a user based on at least a portion of the derived physiological movement signal.

In some versions, the medium may further include processor-executable instructions to conduct biometric recognition of a user based on at least a portion of the derived physiological movement signal. The medium may further include processor-executable instructions to generate a communication over a network based on (a) a biometric evaluation determined from an analysis of at least a portion of the derived physiological movement signal, and/or (b) a detected presence determined from an analysis of at least a portion of the derived physiological movement signal. The medium may further include processor-executable instructions configured to cause the interactive audio device to acoustically detect motion presence of a user, audibly challenge the user, audibly authenticate the user, and authorize the user or communicate an alarm message about the user. The processor-executable instructions to audibly authenticate the user may be configured to compare a verbal sound wave of the user sensed by the microphone with a previously recorded verbal sound wave. Optionally, the processor-executable instructions may be configured to authenticate the user with motion-based biometric sensing.

In some versions, the medium may include processor-executable instructions to cause the interactive audio device to detect a motion gesture based on at least a portion of the derived physiological movement signal. The medium may include processor-executable instructions to generate a control signal, based on the detected motion gesture, to send a notification, or to control a change to an operation of (a) an automated appliance and/or (b) the interactive audio device.

The control signal to control the change to the operation of the interactive audio device may effect activating microphone sensing for initiating interactive voice assistant operations of the interactive audio device, whereby an inactive interactive voice assistant process may be engaged. The initiating the interactive voice assistant operations may be further based on detection of a verbal keyword by the microphone sensing. The medium may include processor-executable instructions to cause the interactive audio device to detect respiratory motion of a user based on at least a portion of the derived physiological movement signal and generate output cues to motive the user to adjust user breathing.

In some versions, the medium may include processor-executable instructions to cause the interactive audio device to receive a communication from another interactive audio device, controlled by another processing device via inaudible sound waves sensed by the microphone of the interactive audio device. The instructions to control producing the sound signal in a vicinity of the interactive audio device may adjust parameters for producing at least a portion of the sound signal based on the communication. The adjusted parameters reduce interference between the interactive audio device and the another interactive audio device. The evaluation of at least a portion of the derived physiological movement signal further may include a detection of sleep onset or wake onset, and wherein the output based on the evaluation may include a service control signal. The service control signal may include one or more of: a lighting control; an appliance control; a volume control; a thermostat control; and a window covering control. The medium may further include processor-executable instructions to prompt a user for collecting feedback and to generate advice in response based on at least one of a portion of the derived physiological movement signal and the feedback. The medium may include processor-executable instructions to determine environmental data, and wherein the advice may be further based on the determined environmental data. The medium may include processor-executable instructions to determine environmental data, and to generate a control signal for an environmental control system based on the determined environmental data and at least a portion of the derived physiological movement signal. The medium may include processor-executable instructions to provide a sleep improvement service, the sleep improvement service may include any of: (a) generating advice in response to detected sleep condition and/or collected user feedback; and (b) generating control signals to control environmental appliances to set environmental sleep conditions and/or provide a sleep related advice message to the user.

In some versions, the medium may include processor-executable instructions to detect a gesture based on at least a portion of the derived physiological movement signal and to initiate microphone sensing for initiating interactive voice assistant operations of the interactive audio device. The medium may include processor-executable instructions to initiate and monitor a nap session based on at least a portion of the derived physiological movement signal. The medium may include processor-executable instructions to vary a detection range by varying parameters of at least a portion of the produced sound signal to track movement of a user through the vicinity. The medium may include processor-executable instructions to detect unauthorized movement with at least a portion of the derived physiological movement signal and generate an alarm or a communication to notify the user or a third party. The communication may provide an alarm on a smart phone or smart watch.

Some versions of the present technology may include a server. The server may have access to any processor-readable medium as described herein. The server may be configured to receive requests for downloading the processor-executable instructions of the processor-readable medium to an interactive audio device over a network.

Some versions of the present technology may include an interactive audio device. The interactive audio device may include: one or more processors. The interactive audio device may include a speaker coupled to the one or more processors. The interactive audio device may include a microphone coupled to the one or more processors. The interactive audio device may include any processor-readable medium describes herein and/or the one or more processors may be configured to access the processor-executable instructions with any of the server(s) described herein. Optionally, the interactive audio device may be a portable and/or a hand-held device. The interactive audio device may include a mobile phone, a smart watch, tablet computer, or a smart speaker.

Some versions of the present technology may include a method of a server having access to any of the processor-readable medium(s) described herein. The method may include receiving, at the server, a request for downloading the processor-executable instructions of the processor-readable medium to an interactive audio device over a network. The method may include transmitting the processor-executable instructions to the interactive audio device in response to the request.

Some versions of the present technology may include a method of a processor of an interactive audio device. The method may include accessing, with a processor, any processor-readable medium described herein. The method may include executing, in the processor, the processor-executable instructions of the processor-readable medium.

Some versions of the present technology may include a method of an interactive audio device to detect physiological movement of a user. The method may include producing, via a speaker coupled to the interactive audio device, a sound signal in a vicinity of the interactive audio device. The method may include sensing, via a microphone coupled to the interactive audio device, a reflected sound signal from the vicinity. The method may include deriving, in a processor, a physiological movement signal with at least a portion of the reflected sound signal and a signal representative of at least a portion of the sound signal. The method may include generating from the processor an output based on an evaluation of at least a portion of the derived physiological movement signal.

In some versions, at least a portion of the produced sound signal, such as the portion used for sensing, may be in an substantially inaudible sound range. The portion of the produced sound signal may be a low frequency ultrasonic acoustic signal. The signal representative of the portion of the sound signal may comprise an internally generated oscillator signal or a direct path measured signal. The method may include deriving the physiological movement signal (a) with at least portion of the produced sound signal and the portion of the sensed reflected sound signal or (b) with the portion of the sensed reflected sound signal and an associated signal that may be associated with the at least a portion of the produced sound signal. Optionally, the associated signal may be an internally generated oscillator signal or a direct path measured signal. The method may include deriving the physiological movement signal by multiplying an oscillator signal with the portion of the sensed reflected sound signal. The method may include evaluating, in a processor, via the microphone coupled to the interactive audio device, a sensed audible verbal communication, wherein generating the output may be in response to the sensed audible verbal communication. The method may include deriving the physiological movement signal by demodulating the portion of the sensed reflected sound signal with at least a portion of the sound signal. The demodulating may include a multiplication of the portion of the sound signal and the portion of the sensed reflected sound signal. The producing the sound signal may generates a dual tone frequency modulated continuous wave signal. The dual tone frequency modulate continuous wave signal may include a first sawtooth frequency change overlapped with a second sawtooth frequency change in a repeated waveform. The method may include may include generating an ultra-wide band (UWB) sound signal as audible white noise, and wherein user motion may be detected with the UWB sound signal. The method may include generating, in a setup process, probing acoustic sequences from the speaker to calibrate distance measurement of low frequency ultrasonic echoes.

In some versions, the method may include generating, in a setup process, time synchronized calibration acoustic signals from one or more speakers, including the speaker, to estimate a distance between the microphone and another microphone of the interactive audio device. The method may include operating a beam forming process to further localize a detected area. Optionally, the generated output based on the evaluation of at least a portion of the derived physiological movement signal may include monitored user sleep information. The evaluation of at least a portion of the derived physiological movement signal may include detecting one or more physiological parameters. The one or more physiological parameters may include any one or more of breathing rate, relative amplitude of breathing, heart rate, cardiac amplitude, relative cardiac amplitude, and heart rate variability. The monitored user sleep information may include any of a sleep score, a sleep stage and a time in a sleep stage. The generated output may include an interactive query and response presentation. The generated interactive query and response presentation may be effected by way of a speaker. The generated interactive query and response presentation may include advice to improve monitored user sleep information.

In some versions, the generated output based on the evaluation of at least a portion of the derived physiological movement signal may be further based on accessing a server on a network and/or conducting a search of a network resource. The search may be based on historic user data. The generated output based on at least a portion of the evaluation of the derived physiological movement signal may include a control signal to control an automated appliance or a system. The method may further include transmitting the control signal to the automated appliance or system over a network. The network may be an internet. The method may further include generating, in the processor, a control signal to change a setting of the interactive audio device based on an evaluation of at least a portion of the derived physiological movement signal. The control signal to change a setting of the interactive audio device may include a change in volume based on a detection of user distance from the interactive audio device, a user's state or user's location. The method may further include evaluating, in the processor, motion characteristics of different acoustic sensing ranges to monitor sleep characteristics of a plurality of users.

The method may further include controlling producing simultaneous acoustic sensing signals at different sensing frequencies for sensing different users with different frequencies. The method may include controlling producing interleaved acoustic sensing signals for sensing different users at different times. The method may include detecting presence or absence of a user based on at least a portion of the derived physiological movement signal. The method may include conducting, with the processor, biometric recognition of a user based on at least a portion of the derived physiological movement signal. The method may include generating, with the processor, a communication over a network based on (a) a biometric evaluation determined from an analysis of at least a portion of the derived physiological movement signal, and/or (b) a detected presence determined from an analysis of at least a portion of the derived physiological movement signal. The method may include, with the interactive audio device, acoustically detecting motion presence of a user, audibly challenging the user, audibly authenticating the user, and authorizing the user or communicating an alarm message about the user. Optionally, audibly authenticating the user may include comparing a verbal sound wave of the user sensed by the microphone with a previously recorded verbal sound wave. The method may include authenticating the user with motion-based biometric sensing.

In some versions, the method may include with the interactive audio device, detecting a motion gesture based on at least a portion of the derived physiological movement signal. The method may include generating, in a processor of the interactive audio device, based on the detected motion gesture, a control signal to send a notification, or to control a change to an operation of (a) an automated appliance and/or (b) the interactive audio device. The control signal to control the change to the operation of the interactive audio device may include activating microphone sensing for initiating interactive voice assistant operations of the interactive audio device, whereby an inactive interactive voice assistant process may be engaged. The method may include initiating the interactive voice assistant operations based on detection of a verbal keyword by the microphone sensing. The method may include, with the interactive audio device, detecting respiratory motion of a user based on at least a portion of the derived physiological movement signal and generating output cues to motive the user to adjust user breathing. The method may include, with the interactive audio device, receiving a communication from another interactive audio device, controlled by another processing device via inaudible sound waves sensed by the microphone of the interactive audio device. The method may include adjusting parameters for producing at least a portion of the sound signal in a vicinity of the interactive audio device based on the communication. The adjusting parameters may reduce interference between the interactive audio device and the other interactive audio device. The evaluation of at least a portion of the derived physiological movement signal further may include detecting sleep onset or wake onset, and wherein the output based on the evaluation may include a service control signal. The service control signal may include one or more of: a lighting control; an appliance control; a volume control; a thermostat control; and a window covering control.

The method may include prompting a user for collecting feedback and to generate advice in response based on at least one of the derived physiological movement signal and the feedback. The method may include determining environmental data, and wherein the advice may be further based on the determined environmental data. The method may include determining environmental data, generating a control signal for an environmental control system based on the determined environmental data and at least a portion of the derived physiological movement signal. The method may further include controlling providing a sleep improvement service, the sleep improvement service may include any of: (a) generating advice in response to detected sleep condition and/or collected user feedback; and (b) generating control signals to control environmental appliances to set environmental sleep conditions and/or provide a sleep related advice message to the user. The method may include detecting a gesture based on the derived physiological movement signal and initiating microphone sensing for initiating interactive voice assistant operations of the interactive audio device. The method may include initiating and monitoring a nap session based on at least a portion of the derived physiological movement signal. The method may include varying a detection range by varying parameters of at least a portion of the produced sound signal to track movement of a user through the vicinity. The method may include detecting unauthorized movement with at least a portion of the derived physiological movement signal and generating an alarm or a communication to notify a third party the user or a third party. The communication provides an alarm on a smart phone or smart watch.

The methods, systems, devices and apparatus described herein can provide improved functioning in a processor, such as of a processor of a general or specific purpose computer, portable computer processing device (e.g., mobile phone, smart watch, tablet computer, smart speaker, smart television etc.), respiratory monitor and/or other processing apparatus utilizing a microphone and speaker. Moreover, the described methods, systems, devices and apparatus can provide improvements in the technological field of automated smart audio devices.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing particular examples discussed and is not intended to be limiting.

The following description is provided in relation to various forms of the present technology that may share common characteristics or features. It is to be understood that one or more features of any one exemplary form may be combinable with one or more features of another form. In addition, any single feature or combination of features in any of form described herein may constitute a further exemplary form.

5.1 Screening, Monitoring, and Detection with Audio Equipment

The present technology concerns audio systems, methods, and apparatus for detecting movement of a subject, including, for example, gross body movement, breathing movement and/or cardiac related chest movement, such as while the subject is asleep. More particularly, a processing application associated with an interactive audio device, such as a smart speaker. In some versions the audio device may be a smartphone, tablet, mobile device, mobile phone, smart television, laptop computer etc. that uses the device sensors, such as a speaker and microphone, to detect such motion.

Figure 1:
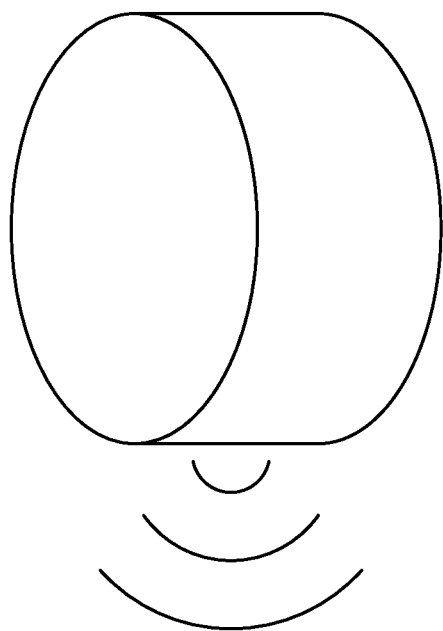
FIG. 1 illustrates an example voice enabled audio device such as one using low frequency ultrasonic biomotion sensing with signal generation and processing techniques described herein.
Figure 1:
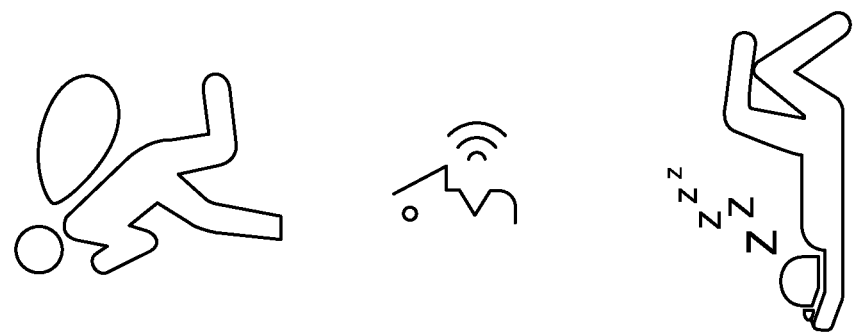
Figure 2:
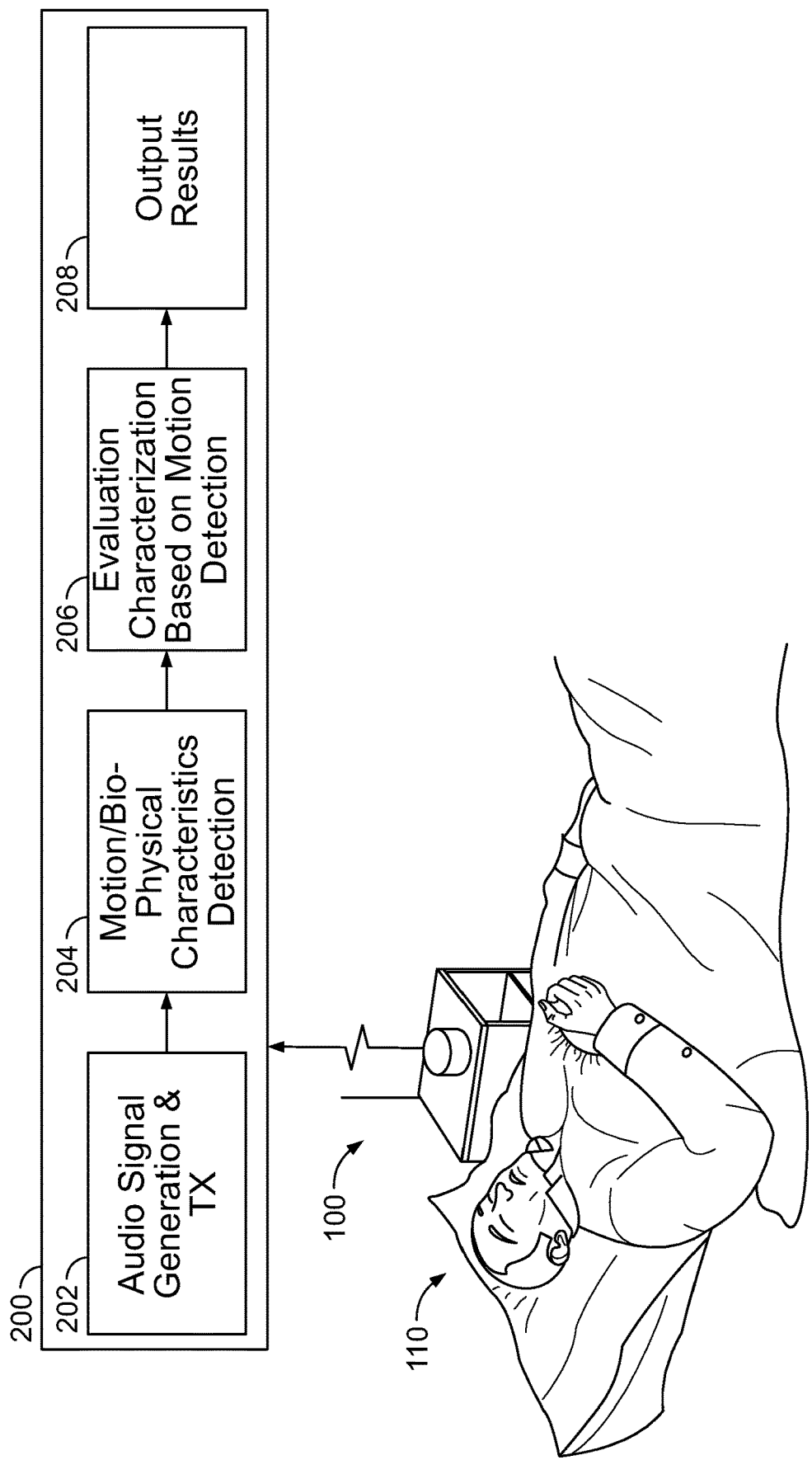
FIG. 2 illustrates an example processing device for receiving audio information from a vicinity of the device and a schematic illustration of example processes of the device.
Figure 3:
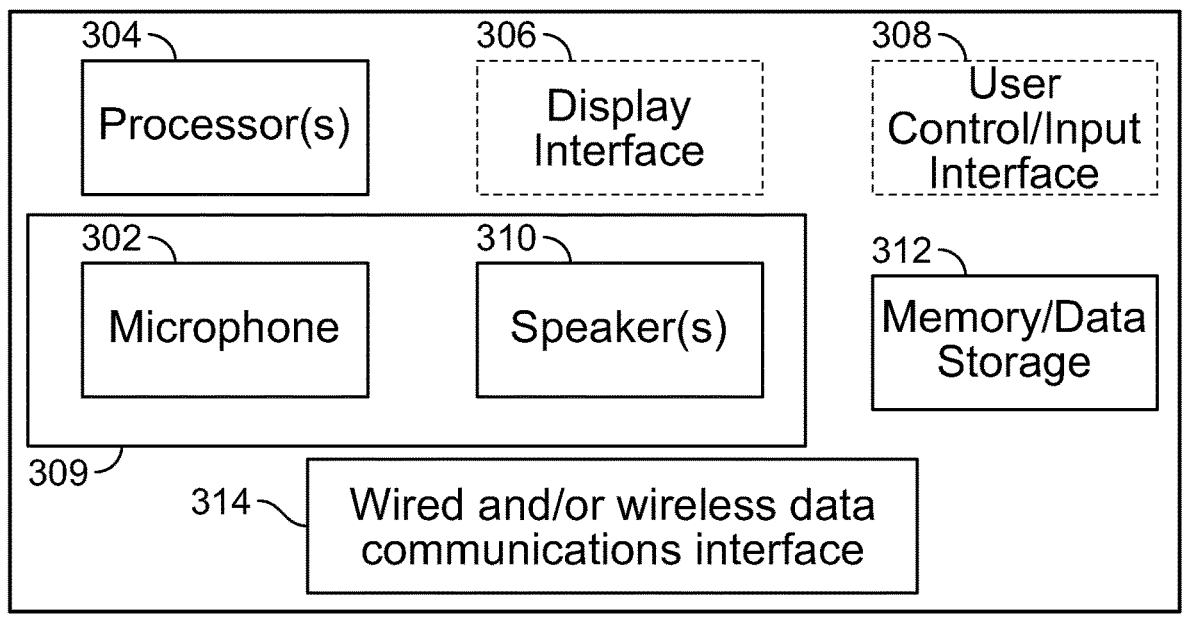
FIG. 3 is schematic illustration of a processing device, such as a smart speaker device, as it may be configured in accordance with some forms of the present technology.

A particularly minimalist or non-obtrusive version of an example system suitable for implementing the present technology is now described with reference to FIGS. 1 to 3. The interactive audio device may be implemented as a processing device 100 having one or more processors, such as a microcontroller, that may be a smart speaker that is configured with an application 200 for detecting movement of subject 110. It may be placed on a bedside table near subject 110 or otherwise be located in a room. Alternatively, processing device 100 may be, for example, a smartphone, tablet computer, laptop computer, smart television or other electronic device. The processor(s) of the processing device 100 may be configured to, among other things, execute the functions of application 200, including causing an audio signal to be generated and transmitted, typically through the air as a generally open or unrestricted medium such as in a room vicinity of the device. The processing device may receive a reflection of the transmitted signal by sensing it with, for example, a transducer such as a microphone. The processing device may process the sensed signal, such as by demodulation with the transmitted signal, to determine body movement such gross body movement, cardiac movement and respiration movement. Processing device 100 will typically comprise, among other components, a speaker and a microphone. The speaker may be implemented to transmit the generated audio signal and the microphone to receive the reflected signal. The generated audio signal for sensing and processing may be implemented with any of the techniques described in International Patent Application PCT/EP2017/073613 filed on Sep. 19, 2017, the entire disclosure of which is incorporated herein by reference. Although the version illustrated in FIGS. 1 to 3 illustrate various processing devices with integrated sensing apparatus (e.g., where a housing includes all of the sensing apparatus or components such as the microphone and speaker), in some versions, the sensing apparatus may be discrete or separately housed components that couple or work together via wired and/or wireless connection(s).

While the sensing apparatus are generally described herein in relation to acoustic sensing (e.g., low frequency ultrasonic sensing), it is understood that the methods and devices may be implemented using other sensing techniques. For example, as an alternative, the processing device may be implemented with a radio frequency (RF) transceiver of an RF sensor to serve as sensing apparatus, such that the generated signal and reflected signal are RF signals. Such a RF sensing device, which may be integrated with or coupled to the processing device, may implemented with any of the techniques and senor components described in International Patent Application No. PCT/US2013/051250, entitled "Range Gated Radio Frequency Physiology Sensor" and filed on Jul. 19, 2013; International Patent Application No. PCT/EP2017/070773, entitled "Digital Radio Frequency Motion Detection Sensor" and filed on Aug. 16, 2017; and International Patent Application No. PCT/EP2016/069413, entitled "Digital Range Gated Radio Frequency Sensor" and filed on Aug. 16, 2017. Similarly, in alternative versions, such sensing apparatus for the transmission of a sensing signal and sensing of its reflection may be implemented with an infrared radiation generator and an infrared radiation detector (e.g., an IR emitter and IR detector). The processing of such signals for motion detection and characterization as described herein may be similarly implemented.

Using a combination of two or more of these different sensing techniques, can enhance the sensing outcome by combining the advantages of the respective techniques. For instance, the discussed acoustic sensing technique is quite acceptable in the noisy environment of our daily life. However, a user with very sensitive hearing may find the use of this technique to be problematic at night, when the noise is much lower and the sensing signal is easier to hear. Similarly, whilst an IR sensing provides a good S/N signal during night time, its use may be problematic in the light (and heat) of day. An IR sensing may be used in this case at night, complemented by the use of the acoustic sensing during the day.

Figure 5:
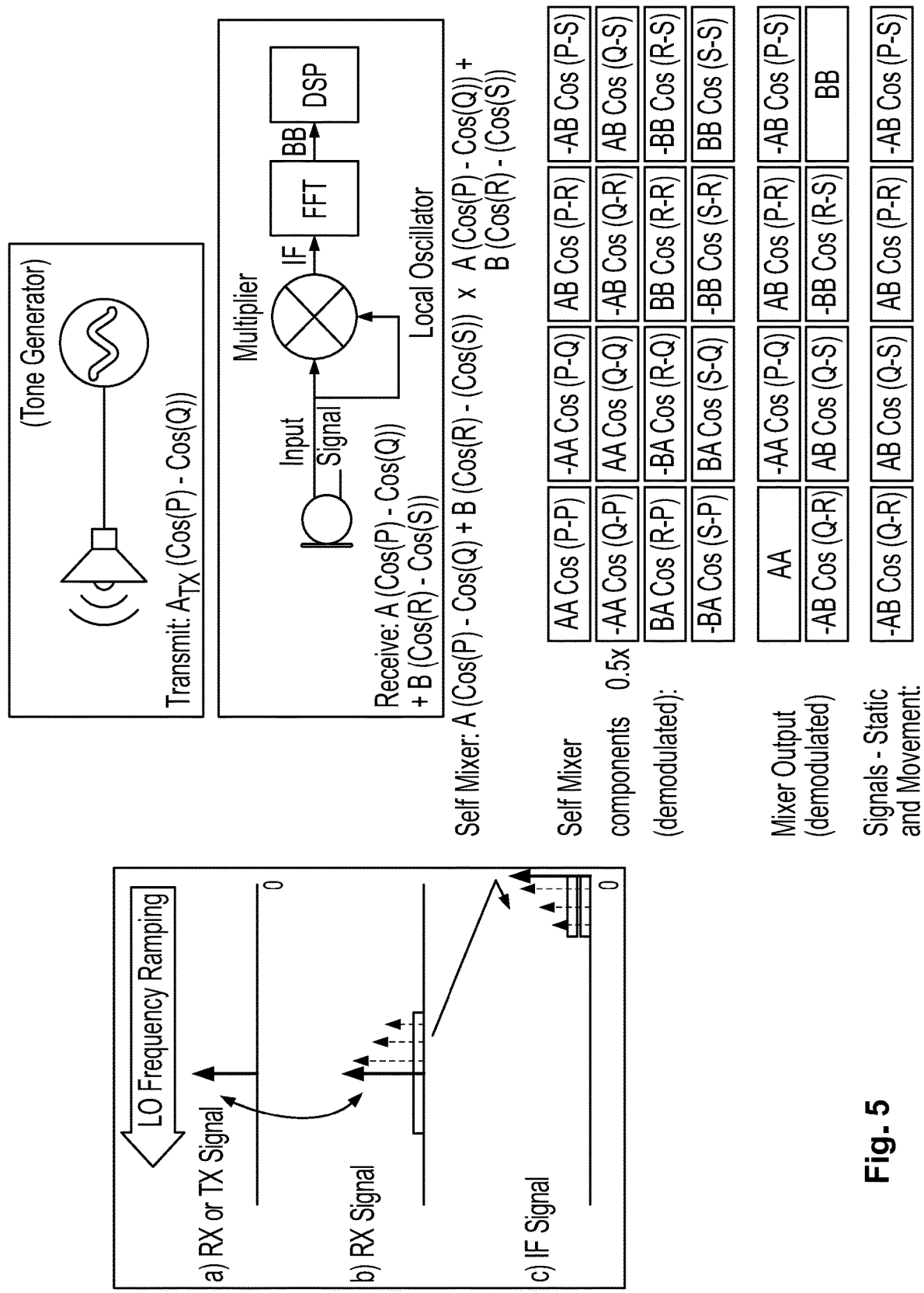
FIG. 5 illustrates example demodulation for a dual tone FMCW that may be implemented for a sensing system of the present technology.

Optionally, the sound-based sensing methodologies of the processing device may be implemented in or by other types of devices such as a bedside device (e.g., a respiratory therapy device such as a continuous positive airway pressure (e.g., "CPAP") device or high flow therapy device) such as the respiratory therapy device 5000 illustrated in FIG. 5 where the therapy device serves as the processing device 100 or works in conjunction with a separate processing device 100. Examples of such devices, including a pressure device or blower (e.g., a motor and impeller in a volute), one or more sensors and a central controller of the pressure device or blower, may be considered in reference to the devices described in International Patent Publication No. WO/2015/061848 (Appl. No. PCT/AU2014/050315) filed on Oct. 28, 2014, and International Patent Publication No. WO/2016/145483 (Appl. No. PCT/AU2016/050117) filed on Mar. 14, 2016, the entire disclosures of which are incorporated herein by reference. Such a respiratory therapy device 5000 may include an optional humidifier 4000 and provide therapy to a patient interface 3000 via a patient circuit 4170 (e.g., a conduit). In some cases, the respiratory therapy device 5000 might have a separate sensor, such as a microphone, for sensing internal sound-related conditions within and through the patient circuit 4170, as opposed to serving to sense the externally sound related acoustic conditions of the processes described throughout this application.

Processing device 100 may be adapted to provide an efficient and effective method of monitoring a subject's breathing and/or other movement related characteristics. When used during sleep, the processing device 100 and its associated methods can be used to detect, for example, the user's breathing and identify sleep stages, sleep states, transitions between states, breathing and/or other respiratory characteristics. When used during wake, the processing device 100 and its associated methods can be used to detect movement such as presence or absence of a person or subject breathing (inspiration, expiration, pause, and derived rate) and/or ballistocardiogram waveform and subsequent derived heart rate, etc. Such movement or movement characteristics may be used for controlling various functions as described herein in more detail.

Processing device 100 may include integrated chips, a memory and/or other control instruction, data or information storage medium. For example, programmed instructions encompassing the assessment/signal processing methodologies described herein may be coded on integrated chips in the memory of the device or apparatus to form an application specific integrated chip (ASIC). Such instructions may also or alternatively be loaded as software or firmware using an appropriate data storage medium. Optionally, such processing instructions may be downloaded such as from a server over a network (e.g. an internet) to the processing device such that when the instructions are executed, the processing device serves as a screening or monitoring device.

Accordingly, processing device 100 may include a number of components as illustrated by FIG. 3. The processing device 100 may include, among other components, a microphone(s) or sound sensor 302, a processor(s) 304, an optional display interface 306, an optional user control/input interface 308, a speaker(s) 310, and a memory/data storage 312, such as with the processing instructions of the processing methodologies/modules described herein. In some cases, the microphone and/or speaker may serve as the user interface with the processor(s) of the device, such as to control operations of the processing device, for example, when the processing device responds, such as via the speaker, to audio and/or verbal commands sensed by the microphone. In this regard, the processing device 100 may serve as a voice assistant such as using natural language processing.

One or more of the components of processing device 100 may be integral with or operably coupled with processing device 100. For example, microphone(s) or sound sensor 302 may be integral with processing device 100 or coupled with processing device 100 such as through a wired or wireless link (e.g., Bluetooth, Wi-Fi etc.). Thus, the processing device 100 may include a data communications interface 314.

Memory/data storage 312 may comprise a plurality of processor control instructions for controlling processors 304. For example, memory/data storage 312 may comprise processor control instructions for causing application 200 to be performed by the processing instructions of the processing methodologies/modules described herein.

Examples of the present technology may be configured to use one or more algorithms or processes, which may be embodied by application(s) 200, to detect motion, breathing, and optionally sleep characteristics while a user is asleep using the processing device 100. For example, application 200 may be characterized by several sub-processes or modules. As shown in FIG. 2, application 200 may include an audio signal generation and transmission sub-process 202, a motion and bio-physical characteristic detection sub-process 204, a motion characterization sub-process 206 such as for subject absence/presence detection, biometric identification, sleep characterization, respiratory or cardiac related characterizations etc., and a results output sub-process 208, such as for presenting information or controlling various devices as described in more detail herein.

For example, optional sleep staging at processing 206, such as in a sleep staging processing module may be implemented. However, any one or more of such processing modules/blocks may optionally be added (e.g., sleep scoring or staging, subject recognition processing, motion monitoring and/or prediction processing, appliance control logic processing, or other output processing, etc.). In some cases, the functions of signal post-processing at may be performed using any of the components, devices and/or methodologies of the apparatus, system and method described in any of the following patents or patent applications, wherein the entire disclosures of each is incorporated by reference herein: International Patent Application No. PCT/US2007/070196, filed Jun. 1, 2007 and entitled "Apparatus, System, and Method for Monitoring Physiological Signs;" International Patent Application No. PCT/US2007/083155, filed Oct. 31, 2007, entitled "System and Method for Monitoring Cardio-Respiratory Parameters;" International Patent Application No. PCT/US2009/058020, filed Sep. 23, 2009, entitled "Contactless and Minimal-Contact Monitoring of Quality of Life Parameters for Assessment and Intervention;" International Application No. PCT/US2010/023177, filed Feb. 4, 2010, entitled "Apparatus, System, and Method for Chronic Disease Monitoring;" International Patent Application No. PCT/AU2013/000564, filed Mar. 30, 2013, entitled "Method and Apparatus for Monitoring Cardio-Pulmonary Health;" International Patent Application No. PCT/AU2015/050273, filed May 25, 2015, entitled "Methods and Apparatus for Monitoring Chronic Disease;" International Patent Application No. PCT/AU2014/059311, filed Oct. 6, 2014, entitled "Fatigue Monitoring and Management System;" International Patent Application no. PCT/EP2017/070773, filed on Aug. 16, 2017, entitled "Digital Radio Frequency Motion Detection Sensor"; International Patent Application No. PCT/AU2013/060652, filed Sep. 19, 2013, entitled "System and Method for Determining Sleep Stage;" International Patent Application No. PCT/EP2016/058789, filed Apr. 20, 2016, entitled "Detection and Identification of a Human from Characteristic Signals;" International Patent Application No. PCT/EP2016/080267, filed on Dec. 8, 2016, entitled "Periodic Limb Movement Recognition with Sensors"; International Patent Application No. PCT/EP2016/069496, filed 17 Aug. 2016, entitled "Screener for Sleep Disordered Breathing;" International Patent Application No. PCT/EP2016/058806, filed on Apr. 20, 2016, "Gesture Recognition with Sensors"; International Patent Application No. PCT/EP2016/069413, filed Aug. 16, 2016, entitled "Digital Range Gated Radio Frequency Sensor;" International Patent Application No. PCT/EP2016/070169, filed Aug. 26, 2016, entitled "Systems and Methods for Monitoring and Management of Chronic Disease;", International Patent Application No. PCT/US2014/045814, filed Jul. 8, 2014, entitled "Methods and Systems for Sleep Management;" U.S. patent application Ser. No. 15/079,339, filed Mar. 24, 2016, entitled "Detection of Periodic Breathing." Thus, in some examples, the processing of detected movement, including for example, the breathing movement, may serve as a basis for determining any one or more of (a) a sleep state indicating sleep; (b) a sleep state indicating awake; (c) a sleep stage indicating deep sleep; (d) a sleep stage indicating light sleep; and (e) a sleep stage indicating REM sleep. In this regard, while the sound related sensing technologies of the present disclosure provide for different mechanisms/processes for motion sensing such as using a speaker and microphone and processing of the sound signals, when compared to radar or RF sensing technologies as described in some of these incorporated references, once a breathing signal, such as breathing rate is obtained with the sound sensing/processing methodologies described in this specification) the principles of processing breathing or other motion signals for an extraction of sleep states/stages information may be implemented by the determination methodologies of these incorporated references. For example, once the respiration rate and movement and activity counts are determined from motion whether by RF or SONAR, sleep staging is a common analysis. By way of additional example, the sensing wavelengths may be different between an RF pulsed CW and a SONAR FMCW implementation. Thus, velocity may be determined differently such as by detecting movement across a range (different sensing distances). For FMCW, movement detection may be made at multiple ranges. Thus, one or more moving targets may be tracked (whether it is two people, or indeed different parts of a person—depending on their angle with respect to the SONAR sensor).

Typically, an audio signal from a speaker may be generated and transmitted towards a user for sensing, such as an audio signal using one or more tones described herein. A tone provides pressure variation in a medium (e.g., air) at one or more particular frequencies. For purposes of this description, the generated tones (or audio signals or sound signals) may be referred to as "sound", "acoustic" or "audio" because they may be generated in a like manner to audible pressure waves (e.g., by a speaker). However, such pressure variations and tone(s) should be understood herein to be either audible or inaudible, notwithstanding their characterization by any of the terms "sound", "acoustic" or "audio." Thus, the audio signal generated may be audible or inaudible, wherein the frequency threshold of audibility across the human population varies by age. The signal may be substantially inaudible such that most people cannot discern the sound (e.g., in the range above 18 kHz). The typical "audio frequency" standard range is around 20 Hz to 20,000 Hz (20 kHz). The threshold of higher frequency hearing tends to reduce with age, with middle aged people often unable to hear sounds with frequencies above 15-17 kHz, whereas a teenager may be able to hear 18 kHz. The most important frequencies for speech are approximately in the range 250-6,000 Hz. Speaker and microphone signal responses for typical consumer smartphones are designed to roll off above 19-20 kHz in many cases, with some extending to above 23 kHz and higher (especially where the device supports a sampling rate of greater than 48 kHz such as 96 kHz). Therefore, for most people, it is possible to use signals in the range of 17/18 to 24 kHz and remain inaudible. For younger people that can hear 18 kHz but not 19 kHz, a band of 19 kHz to say 21 kHz could be employed. It is noted that some household pets may be able to hear higher frequencies (e.g., dogs up to 60 kHz and cats up to 79 kHz). A suitable range for the sensing audio signal of the present technology may be in a low ultrasonic frequency range such as 15 to 24 kHz, 18 to 24 kHz, 19 to 24 kHz, 15 to 20 kHz, 18 to 20 kHz or 19 to 20 kHz.

Any of the arrangements and methods of audio sensing, such as with use of low frequency ultrasonic sensing signals, as described in PCT/EP2017/073613 may be implemented by the processing device described herein. However, in some cases, a dual tone FMCW (also referred to as a dual ramp technology) may be implemented as described herein.

Figure 4A:
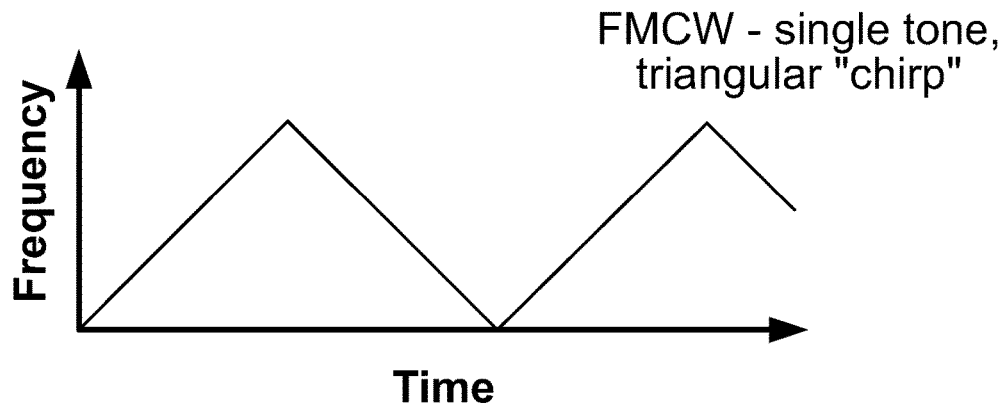
FIG. 4A shows frequency characteristics of a single tone chirp such as for frequency modulated continuous wave sensing (FMCW).

For example, a triangular FMCW waveform with one "tone" (i.e., that is swept up and down in frequency) may be generated by the processing device using its speaker(s) where the waveform has the frequency verses time characteristics illustrated in FIG. 4A, and where processing of the up-sweep, or just the down-sweep, or even both may be evaluated for distance detection. The phase-continuous triangular form for one tone is highly desirable as it minimizes or removes any audible artefact in the played sound created by a phase discontinuity. A ramp variant of this can give rise to a very unpleasant and audible buzzing sound, as the speaker(s) is/are asked to jump from playing a certain amplitude sound at a frequency to a much lower (or much higher) frequency at a similar amplitude within the space of a sample; the mechanical change in the speaker can give rise to a click, and the frequent repetition of the chirp means that the user hears a buzz (many closely spaced clicks).

Alternatively, in some versions of the present technology, the acoustic sensing signal as a FMCW may be implemented with special dual "tones" with a ramp waveform (e.g. which consists of an up-sweep or a down-sweep only)—so that there is a sharp change in frequency from the end of one ramp (frequency ramp up and down) to the next (frequency ramp up and down) without audible artefact. Such a dual "tone" frequency modulated waveform showing its frequency characteristics relative to time in FIG. 4B. This can ultimately simplify the data processing in the system, and also remove the potentially high amplitude transition at each point of a triangular waveform. Sharp and repetitive transitions can sometimes trigger strange behavior in a system's low level DSP/CODEC/firmware).

Figure 4B:
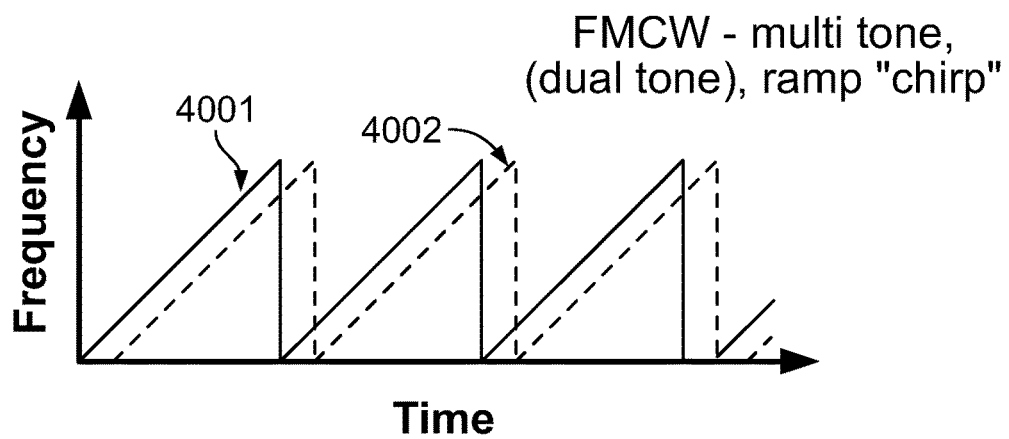
FIG. 4B shows frequency characteristics of a dual tone chirp such as for frequency modulated continuous wave sensing (FMCW).

FIGS. 4A and 4B show a frequency domain comparison of FMCW single tone (FIG. 4A) and dual tone (FIG. 4B) implementations. A single tone (FIG. 4A) may preferentially include a downsweep (a reduction in produced frequency over time) to ensure inaudibility. However, a downsweep may be omitted but may cause some audibility. A dual tone (tone pair) (FIG. 4B) can help avoid the need for such a downsweep, as the time domain representation is shaped such as to be inaudible. FIG. 4B shows the first tone 4001 and the optional second tone 4002 overlap. The figure does not show the received echo (i.e., the reflection signal). Thus, tones form a first sawtooth frequency change overlapped with a second sawtooth frequency change in a repeated waveform. They are continuous such that they may be repeated during a sensing period.

Thus, there are different ways that the acoustic sensing signal can be created when implementing a low frequency ultrasonic sensing system with an FMCW type of approach. This may involve differences in waveform shape in the frequency domain (e.g., triangular (symmetric or asymmetric), ramp, sinusoidal etc.), period (duration of the "chirp" in time), and bandwidth (frequency covered by the "chirp"—e.g., 19-21 kHz). It is also possible to use two or more simultaneous tones in an FMCW configuration.

The choice of number of samples defines a possible output demodulated sampling rate (e.g., a 512 samples at a sampling rate of 48 kHz equates to 93.75 Hz (48,000/512), whereas a 4096 sample duration sweep time equates to 11.72 Hz (48,000/4096). If a triangular waveform is used with a 1500 sample uptime, and 1500 sample downtime, then the output sampling rate is 16 Hz (48,000/3000). For this type of system, synchronization can be performed by multiplying the signal by a reference template, for example.

Regarding the choice of the output sampling rate, empirical testing has shown that operating in the approximate region of 8 to 16 Hz is preferable, as it broadly avoids 1/f noise (low frequency effects due to air movement, potentially strong fading, and/or room modes) as well as staying out of the reverberation region seen at higher demodulated sampling rates (i.e., we have allowed time for the energy in any one frequency of sensing waveform "chirp" to fade before the next similar component in next "chirp"). Presented another way, if you make bins too wide, changes in airflow and temperature (e.g., opening door and heat goes in or out of room) means any block you are looking at could contain an unwanted baseline drift which can look like breathing. Practically, this means that a wave is seen to move across the band (across range bins) as the air moves. This is distinct from more localized effects from a desk or pedestal fan, or an air conditioning or other HVAC system. Effectively, if the blocks are made too wide, the system begins to "look like" a CW system. On the other hand, one can get reverb if the system works at too high a refresh rate (i.e., too short a ramp).

For a triangular FMCW waveform with one "tone" (i.e., that is swept up and down in frequency) as illustrated in FIG. 4A, a system can process, for example, just the up-sweep, or just the down-sweep, or indeed both may be processed for distance detection. The phase-continuous triangular form for one tone is highly desirable as it minimizes or removes any audible artefact in the played sound created by a phase discontinuity. A ramp variant of this can give rise to a very unpleasant and audible buzzing sound, as the speaker(s) is/are asked to jump from playing a certain amplitude sound at a frequency to a much lower (or much higher) frequency at a similar amplitude within the space of a sample; the mechanical change in the speaker can give rise to a click, and the frequent repetition of the chirp means that the user hears a buzz (many closely spaced clicks).

Thus, in some versions of the present technology, the acoustic sensing signal as a FMCW may be implemented with special dual "tones" with a ramp waveform (e.g. which consists of an up-sweep or a down-sweep only)—so that there is a sharp change in frequency from the end of one ramp (frequency ramp up and down) to the next (frequency ramp up and down) without audible artefact. Such a dual "tone" frequency modulated waveform showing its frequency characteristics relative to time, where at least two changing frequency ramps overlap during a period of time and these frequency ramps each may have a different frequency relative to the other(s) at any instant of time in the period such as for the duration of the ramping, is illustrated in FIG. 4B in relation to the dashed line versus the solid line. This can ultimately simplify the data processing in the system, and also remove the potentially high amplitude transition at each point of a triangular waveform. Sharp and repetitive transitions can sometimes trigger strange behavior in a system's low level DSP/CODEC/firmware).

An important consideration to implemented such a dual tone signal is that the resulting shape is made (shaped) such that the speaker/system does not need to make a sharp transition, and it has zero points. This can reduce the need for filtering that would otherwise be implemented to render the signal inaudible. For example, high pass or band pass filtering may be avoided while still permitting the signal to operate as an inaudible sensing signal. The presence of zeros in the waveform eases signal processing because that the zeros simplifies synchronization of the transmit and the receive of such a signal (e.g., for demodulation). A consequence of the dual tones is that it offers an element of fading robustness as more than one tone is used—and fading can vary with the frequency used, as well as phase or frequency (e.g., one might use a 100 Hz offset between the FMCW tones in a dual tone system).

Figure 7:
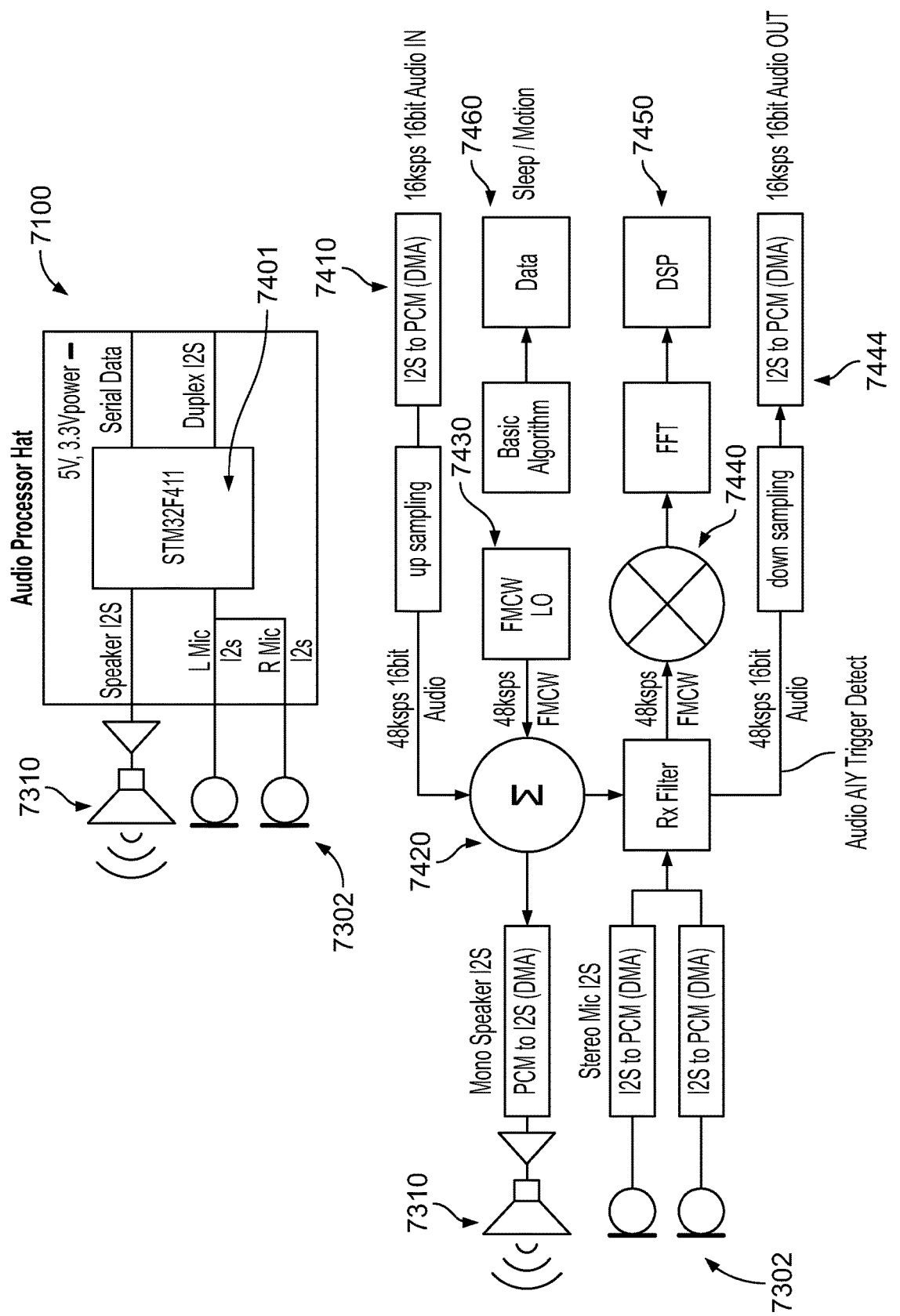
FIG. 7 illustrates example audio processing modules or blocks such as for the processing described herein.
Figure 8:
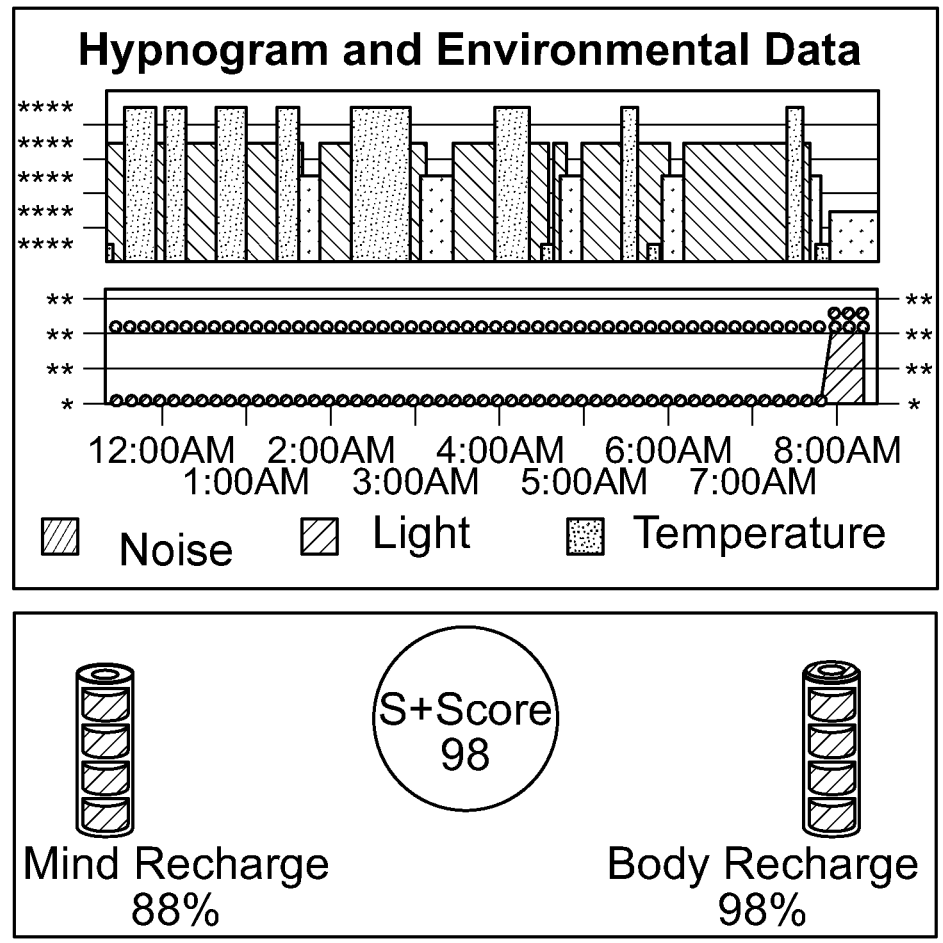
FIG. 8 illustrates example output (e.g., sleep stage data) produced by processing of audio derived motion characteristics.
Figure 8A:
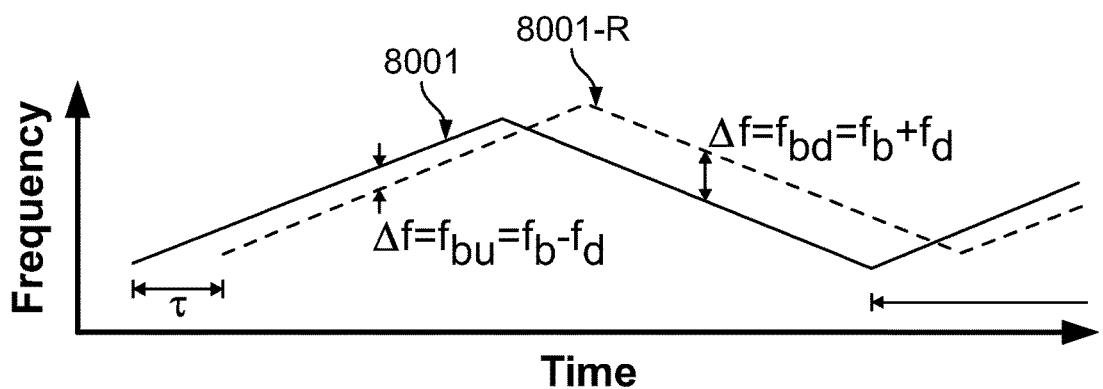
FIGS. 8A, 8B and 8C illustrate various signal characteristics of a triangular single tone such as for a FMCW system.
Figure 8B:
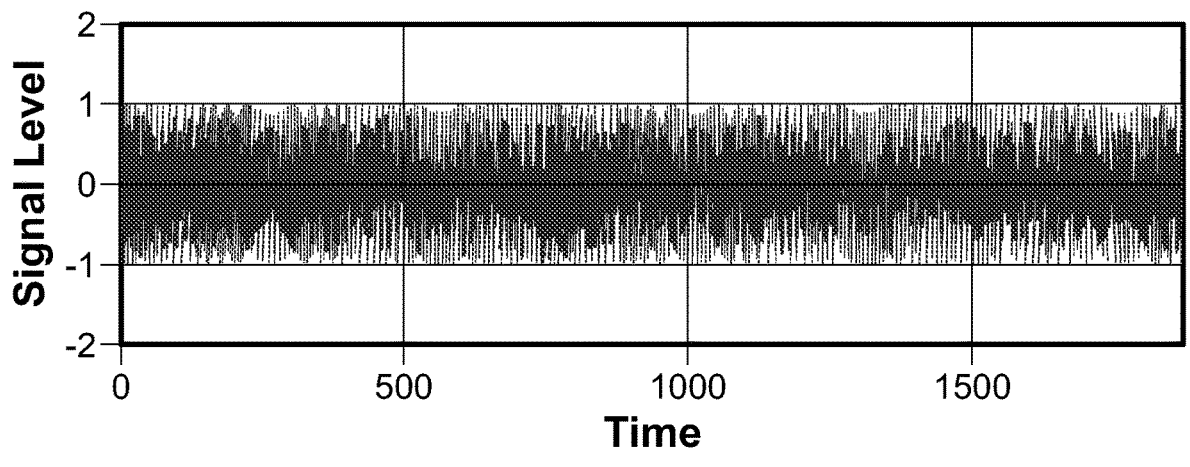
Figure 8C:
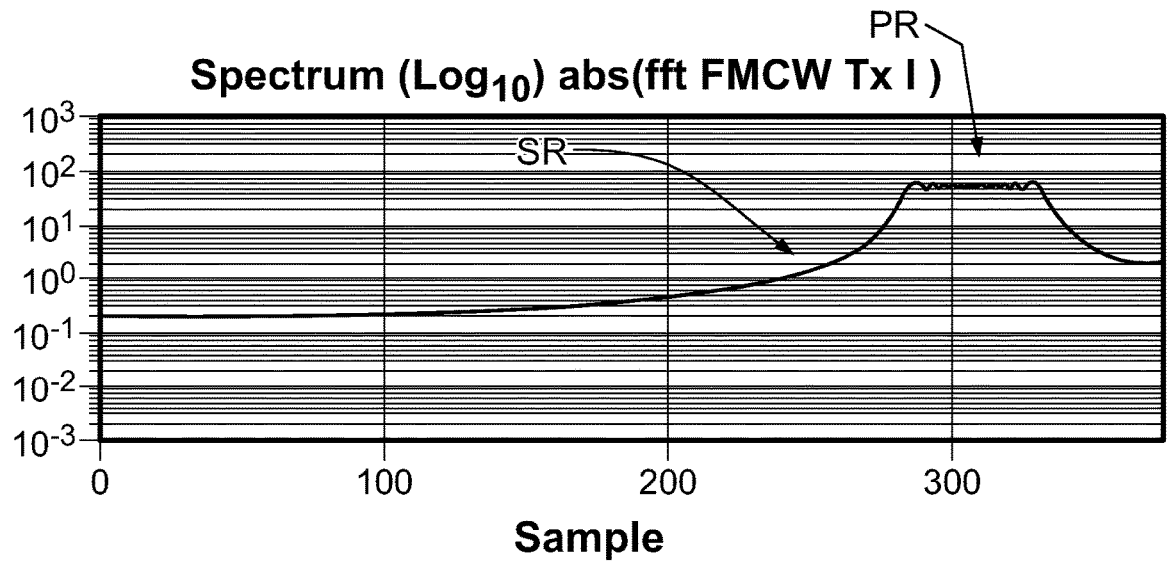
Figure 9A:
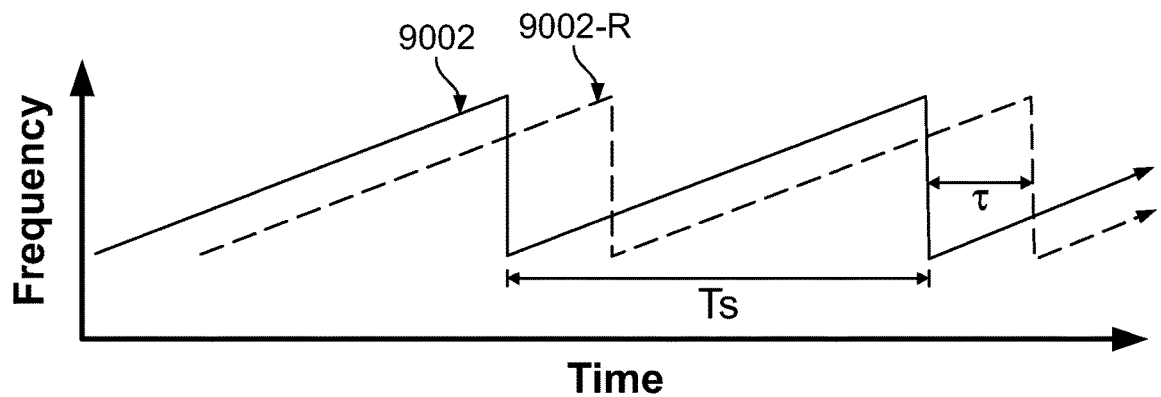
FIGS. 9A, 9B and 9C illustrate various signal characteristics of a triangular dual tone such as for a FMCW system.
Figure 9B:
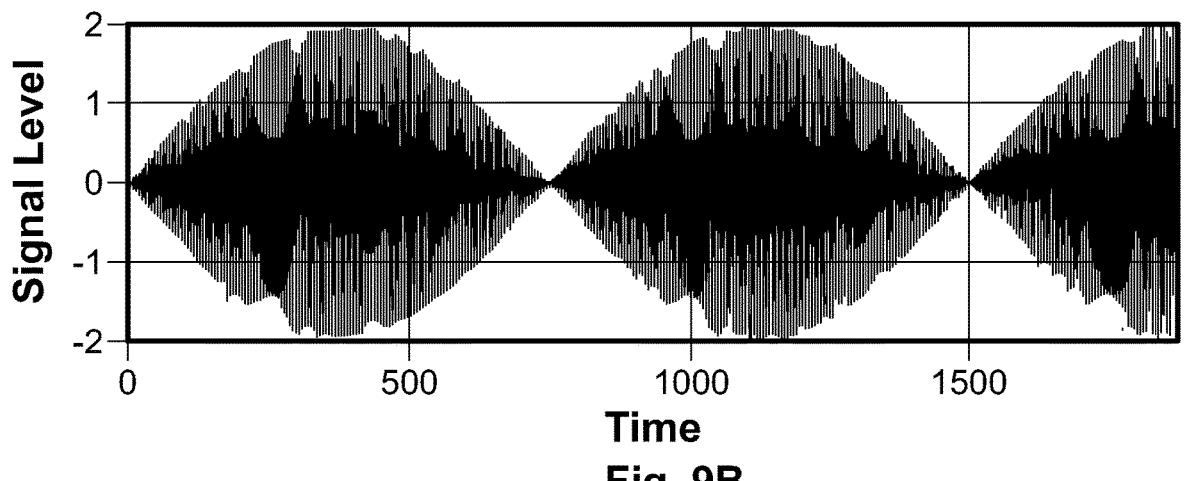
Figure 9C:
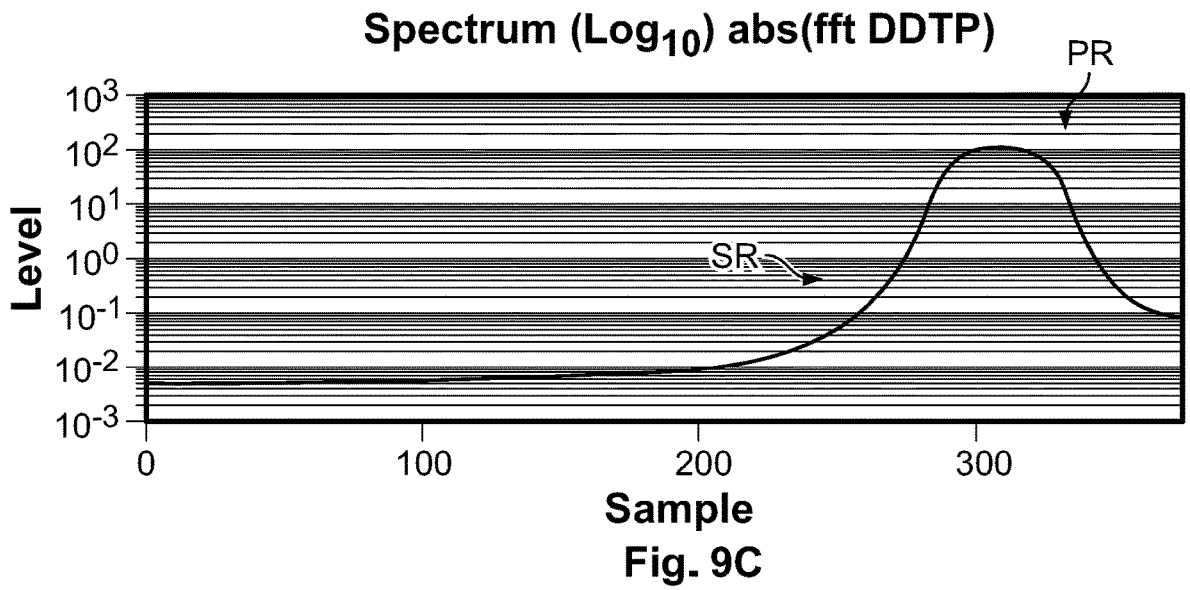

Performance of the FMCW single tone of FIG. 4A and the FMCW dual tone of FIG. 4B may be considered in reference to FIGS. 8 and 9. FIGS. 8A, 8B and 8C show signal characteristics of the FMCW single tone example of FIG. 7A. FIGS. 9A, 9B and 9C show the signal characteristics of the FMCW dual tone example of FIG. 7B.

FIG. 8A shows the transmitted (Tx) signal 8001, and the received (Rx) reflection 8001-R (echo) operating as a triangular single tone FMCW operating in an acoustic sensing system. FIG. 8B shows the time domain waveform. FIG. 8C shows the spectral content of the signal. As evident, there is still content at lower frequencies (outside the peak area relating the bandwidth of the FMCW signal). Such lower frequencies may thus be in an audible frequency range and thereby resulting in an undesirable performance characteristic.

FIG. 9A depicts a dual tone ramp FMCW signal in signal graph 9002. Signal graph 9002 represents both tones, and signal graph 9002-R represents the received echo of the two tones/multi-tone. FIG. 9B shows a cosine-like functional shape of the dual tone, with the zero points (resultant zero crossings). FIG. 9C shows a much smoother peak and lower power amplitude at lower frequencies. The slope region SR of FIG. 9C, when compared to the slope region SR of FIG. 8C, illustrates a sharper decline in power (dB) of the dual tone ramp FMCW in/to the lower frequencies. The sharper roll-off from the range of the high (substantially inaudible, utilised for sensing) frequencies and into the lower (audible, not typically utilised for sensing) frequencies, is a desirable acoustic sensing property as it is less obtrusive for the user. The power at lower frequencies (outside the peak area relating to the bandwidth of the FMCW signal) can be 40 dB less than that in the case of the single tone FMCW triangular form illustrated in FIG. 8C. As illustrated in FIG. 9C, the upper smooth peak region PR of FIG. 9C when compared to the multi-edged peak region PR of FIG. 8C, indicates that the dual tone ramp FMCW signal can have better acoustic sensing properties and is less demanding on the speakers.

Such a multiple tone FMCW or dual tone FMCW system (for example running on a Linux based single board computer) can provide sensing such that it is possible to identify multiple persons within the sensing range of 4 m or more. It can also detect heart rate for example at 1.5 meters from the processing device, and respiration rate(s) at out to approximately 4 meters or more. An exemplar system could use two tones at 18,000 Hz and 18,011.72 Hz, which could ramp to, for example, 19,172 Hz and 19183.72 Hz respectively.

For this ramp of 1,172 Hz, we can consider using, for example, an FFT of size 4096 points, with bin width of 48,000 Hz/4096=11.72. For speed of sound as 340 m/s, we note: 340 ms/s/11.72/2 (for out and back)=14.5 m over 100 bins or 14.5 cm for each bin. Each "bin" can detect up to one person (per bin) for example (but in practice persons would be separated by more than this.) As part of a synchronization process, the signal could be squared, for example, to avoid a more computationally expensive correlation operation, where the signal is multiplied by a reference template. Independent of the FFT size used, the maximum range resolution is speed-of-sound/(Bandwidth*2)=340/(1172*2)=14.5 cm. However, a synchronization process may optionally be provided that includes cross-correlating a sensed reflected signal with a sensed direct path signal. A synchronization process may optionally include multiplying a reference template with at least a portion of the sensed reflected sound signal.

Such a multiple tone FMCW or dual tone FMCW system (for example running on a Linux based single board computer) can provide sensing such that it is possible to identify multiple persons within the sensing range of 4 m or more. It can also detect heart rate for example at 1.5 meters from the processing device, and respiration rate(s) at out to approximately 4 meters or more. An exemplar system could use two tones at 18,000 Hz and 18,011.72 Hz, which could ramp to, for example, 19,172 Hz and 19183.72 Hz respectively.

For this ramp of 1,172 Hz, we can consider using, for example, an FFT of size 4096 points, with bin width of 48,000 Hz/4096=11.72. For speed of sound as 340 m/s, we note: 340 ms/s/11.72/2 (for out and back)=14.5 m over 100 bins or 14.5 cm for each bin. Each "bin" can detect up to one person (per bin) for example (but in practice persons would be separated by more than this.) As part of a synchronization process, the signal could be squared, for example, to avoid a more computationally expensive correlation operation, where the signal is multiplied by a reference template. Independent of the FFT size used, the maximum range resolution is speed-of-sound/(Bandwidth*2)=340/(1172*2)=14.5 cm.

FIG. 5 illustrates an example of "self-mixing" demodulation of a dual tone FMCW ramp by multiplying the signal by itself (squaring). Optionally, demodulation may be carried out by multiplying the received echo signal with a signal representative of the generated transmit signal (e.g., a signal from an oscillator) to produce a signal reflecting distance or motion in the range of the speaker or processing device 100. The processing produces a "beat frequency" signal which is sometimes referred to as an "intermediate" frequency (IF) signal. With FMCW, when the receive Rx signal is demodulated, such as by a local oscillator or by itself as described in more detail herein, and low pass filtered, it may produce an unusual "intermediate" signal that is not yet considered to be baseband. The IF signal may be processed, such as by application of fast Fourier transform processing (FFT), to become baseband (BB).

As illustrated in FIG. 5, the demodulation is conducted with the receive (reflected sound signal) Rx signal only. That is mathematically possible because the Rx signal contains a large percentage of a signal representative of the transmit (Tx) signal (e.g., the produced sound which may, in part, travel a direct path from the speaker to the microphone and be sensed with the reflected sound) in it. The device can multiply the receive signal Rx by itself (such as by just squaring it because demodulation can be considered a multiply operation). This can be followed by a filtering process (e.g. lowpass).

Although FIG. 5 illustrates self-mixing, several different approaches may be implemented to derive a motion signal with the reflected signal, and the sensing signal (i.e., Tx or sound signal). In one such version, a local oscillator LO (which may also produce the sound signal) can effectively produce a copy of the Tx signal for demodulation. The actually produced Tx signal might be slightly different than the internal signal from the oscillator because of delay or distortion. Demodulation can then be conducted by multiplication of the signal from the local oscillator LO(Tx)*Rx which can also be followed by filtering (e.g., lowpass).

In another version, two local oscillators may be implemented to generate two LO signals. For example, a Sin and Cosine copy of the LO signal may be implemented to provide for quadrature demodulation of the receive signal. Typically, only one signal from an oscillator (either Sin or Cosine) is transmitted. The exact Tx signal will be somewhat different from the signal from the local oscillator LO due to delay or distortion. In this version, demodulation may be conducted (a) RX*LO(Sin) and (b) RX*LO(Cos), which may be followed in each case by filtering (e.g., lowpass) to produce both I and Q demodulation components.

Sensing—Mixing (Coexistence) of Acoustic Sensing with Other Audio Playback by the System (Music, Speech, Snoring Etc.)

Some versions of the present technology may be implemented when the processing device 100 may be using its speaker and/or microphone for other purposes, in addition to the ultrasonic sensing described herein. Additional processes may be implemented to permit such simultaneous functioning. For example, the transmit bitstream (acoustic sensing signal) may be digitally mixed with any other audio content (audible) that is being played by the speaker as previously mentioned for simultaneous audio content production and ultrasonic sensing. Several approaches can be used to carry out such audible audio content and ultrasonic processing. One approach requires that the other audio content (which could be mono, stereo or many more channels—such as in many channel surround sound systems) is preprocessed to remove any spectral content that would overlap with the sensing waveform. For example, a music sequence might contain components of over 18 kHz which would overlap with, for example, an 18 to 20 kHz sensing signal. In this case, the music components near 18 kHz can be low pass filtered out. A second option is to adaptively filter the music so as to remove frequency components for the short periods of time during overlapping sensing (direct path and echo), and allow the unfiltered music otherwise; this approach is designed to retain the fidelity of the music. A third option may simply make no changes whatsoever to the music source.

It should be noted that where delays are deliberately added to audio sources on certain channels (e.g., Dolby Pro Logic, Digital, Atmos, DTS etc. or indeed virtualized spatializer functions), any such in-band signals are also accordingly processed, and the sensing waveform will either not be delayed or the delay would be allowed for, when processing the echoes).

Sensing—Coexistence with Voice Assistants

It should be noted that certain realizations of ultrasonic sensing waveforms (e.g., triangular FMCW), may have an unintended and unwanted impact on certain voice assistants that are performing voice recognition services, such as Google Home, as they have spectral content within the audible band. Such potential cross talk can be avoided by using a dual ramp tone pair, or pre-filtering (high pass or band pass filtering the triangular chirp) the sensing waveform, or adapting the voice recognition signal processing to be robust to the ultrasonic sensing signal components.

Consider an FMCW ramp signal y as follows:

$$y=[A\ \text{Cos}(2pi(f_1+f_2t)t+phi]_0^T$$

This ramp from frequency f_1 to frequency f_2 in a time period T. This has sub harmonics as it is switched at a time period of T.

An analysis of this shows that it has out of band harmonics which appear at lower frequencies and so can be heard.

Now consider a specific dual ramp pair y as follows:

$$y[A\ \text{Cos}(2pi(f_1+f_2t)t+phi]_0^T - [A\ \text{Cos}(2pi(f_1+(1/T)+f_2t)\ t+phi]_0^T$$

Thus, the sub-harmonics are cancelled (subtracted in the above), and the signal retained. The 1/T is very specific; by using (1/T), or indeed −(1/T), the effect of the switching at time period T is canceled out. Thus, the resulting signal is inaudible. It does this while being mathematically simple, which is an advantage as it is not computationally onerous on a device (e.g., a smart mobile phone device).

Because the dual tone switches at DC level ("0"), there is a natural point in the waveform chirp (a beginning and an end of the signal) to turn off, such as to avoid clicking (i.e., turn on and off in a way to avoid a loudspeaker making a big jump). The "0"'s also allow us to introduce a quiet period between each chirp, or indeed between groups of chirps, in order to mitigate reverberation—and/or to identify a specific transmitter (i.e., to overlay a sequence of on/off chirp times).

The lack of sub-harmonics is also an advantage as it removes a possible source of interference when considering two devices operating in a room at the same time. Thus, two different devices can use non-overlapping (in frequency) tone pairs—or indeed overlapping in frequency (but not in time—due to the addition of non-overlapping quiet periods) tone pairs. The latter can be an advantage where loudspeaker/microphone combinations have limited available inaudible bandwidth (i.e., their sensitivity rolls off severely over 19 or 20 kHz).

Even comparing a relatively inaudible triangular FMCW signal to a dual tone ramp, the latter has a very much smaller level of sub harmonics (approaching the noise floor on a real world smart device—e.g., near the quantization level).

Because a dual tone ramp can be ramped up or down (rather than triangular) and yet have no out of band components, there are no inter ramp bleed problems which can occur with a triangular ramp.

A standard ramp audio signal cannot be made inaudible without extensive filtering, which would potentially distort the phase and amplitude of the resulting waveform.

Sensing—Calibration/Room Mapping to Optimize Performance

The processing device may be configured with a set-up process. When the device is first set up (or periodically during operation) it can send out an acoustic probing sequence to map the room environment, the presence and/or number of people in the room etc. The process can be repeated if the device is subsequently moved, or the quality of the sensed signals is detected to have decreased. The system may also emit acoustic training sequences in order to check the capabilities of the speaker(s) and mic(s), and estimate equalization parameters; real world transducers may have some non-linearities in the ultrasound frequencies used by the system, as well as temperature and turn on characteristics (e.g., as a loud speaker may take several minutes to settle).

Sensing—Beam Forming for Localization

It is possible to implement dedicated beam forming or utilise existing beam forming functionality—i.e., where signal processing is employed to provide directional or spatial selectivity of signals sent to, or received from, an array of sensors. This is typically a "far field" problem where the wavefront is relatively flat for low frequency ultrasound (as opposed to medical imaging, which is "near field"). For a pure CW system, audio waves travel out from the speaker, leading to areas of maxima and minima. However, if multiple transducers are available, it becomes possible to control this radiation pattern to our advantage—an approach known as beam forming. On the receive side, multiple microphones can also be used. This allows the acoustic sensing to be preferentially steered (e.g., steering the emitted sound and/or the received sound waves where there are multiple speakers) in a direction, and swept across a region. For the case of a user in bed, the sensing can be steered towards the subject—or towards multiple subjects where there are, for example, two persons in the bed. Beam steering can be implemented on transmit or receive. As low cost ultrasonic transducers (microphone or speaker) can be quite directional (e.g., for a small transducer, where the wavelength is comparable to the size of the transducer), this can restrict the area in which they can be steered over.

Sensing—Demodulation and Down Conversion

Returning to FIG. 5, the sensed signal is demodulated, such as with the multiplier (mixer) module 7440 shown in FIG. 7 or according to the demodulator of FIG. 5, to produce a baseband signal that may be further processed to detect whether there is "presence" in the sensing field—a disturbance in the demodulated signal that relates to a change in the echoes received, related to a characteristic motion of a person. Where there is a strong received "direct path" (high crosstalk from speaker to microphone, e.g., transmission through a solid versus through air and/or short distance from speaker to mic) signal, in addition to the received echo signal, multiplication of the resulting sum can be performed to demodulate. Otherwise, the received echo can be multiplied (mixed) with a portion of the originally transmit signal, which is extracted in an electronic, and not acoustic, form. In this specific example, the system is not multiplying the receive signal by the transmit signal to demodulate it (although it may other embodiments). Instead, the system may multiply the receive signal (which contains an attenuated version of the transmit signal, as well as the receive echo (es)) by itself as follows:

Transmit=$A_{TX}$ (Cos (P)–Cos (Q))

Receive=$A$ (Cos (P)–Cos (Q))+$B$ (Cos (R)–Cos (S))

Self mixer=[$A$ (Cos(P)–Cos (Q))+$B$ (Cos(R)–Cos (S))]×[$A$ (Cos (P)–Cos (Q))+$B$ (Cos (R)–Cos (S))] i.e., receive×receive Self Mixer components (Demodulated) after low pass filtering:

| 0.5x | AA Cos (P-P) | –AA Cos (P-Q) | AB Cos (P-R) | –AB Cos (P-S) |
|---|---|---|---|---|
| | –AA Cos (Q-P) | AA Cos (Q-Q) | –AB Cos (Q-R) | AB Cos (Q-S) |
| | BA Cos (R-P) | –BA Cos (R-Q) | BB Cos (R-R) | –BB Cos (R-S) |
| | –BA Cos (S-P) | BA Cos (S-Q) | –BB Cos (S-R) | BB Cos (S-S) |

Self Mixer Output (Demodulated) after equation simplification:

| AA | –AA Cos (P-Q) | AB Cos (P-R) | –AB Cos (P-S) |
|---|---|---|---|
| –AB Cos (Q-R) | AB Cos (Q-S) | –BB Cos (R-S) | BB, | where AA and BB are DC components

Demodulated components that contain reflected signal information (can be static as well as movement related):

| –AB Cos (Q-R) | AB Cos (Q-S) | AB Cos (P-R) | –AB Cos (P-S) |
|---|---|---|---|

The advantages of this are: no synchronization is required between transmit and receive, as all timing information is contained in the receive only, and it is computationally fast and simple (square an array).

After I, Q (in phase and quadrature) demodulation, there is a choice of how to separate the low frequency components relating to air turbulence, multi-path reflections (including fading related to same) and other slow moving (generally non-physiological) information. In some cases, this processing can be called clutter removal. The DC level (mean) can be subtracted, or some other detrending (such as linear trend removal) performed on an overlapping or non-overlapping block basis; a high pass filter can also be applied to remove DC and very low frequency components (VLF). The "removed" information can be processed to estimate the intensity of such DC and VLF data—such as whether there are strong air currents, or significant multipath effects. The filtered demodulated signal can then be passed to a spectral analysis stage. The other choice is not to use high pass filters and to pass the unfiltered signal directly to the spectral analysis processing block, and carry out the DC and VLF estimation at this stage.

Example System Architecture

Figure 6:
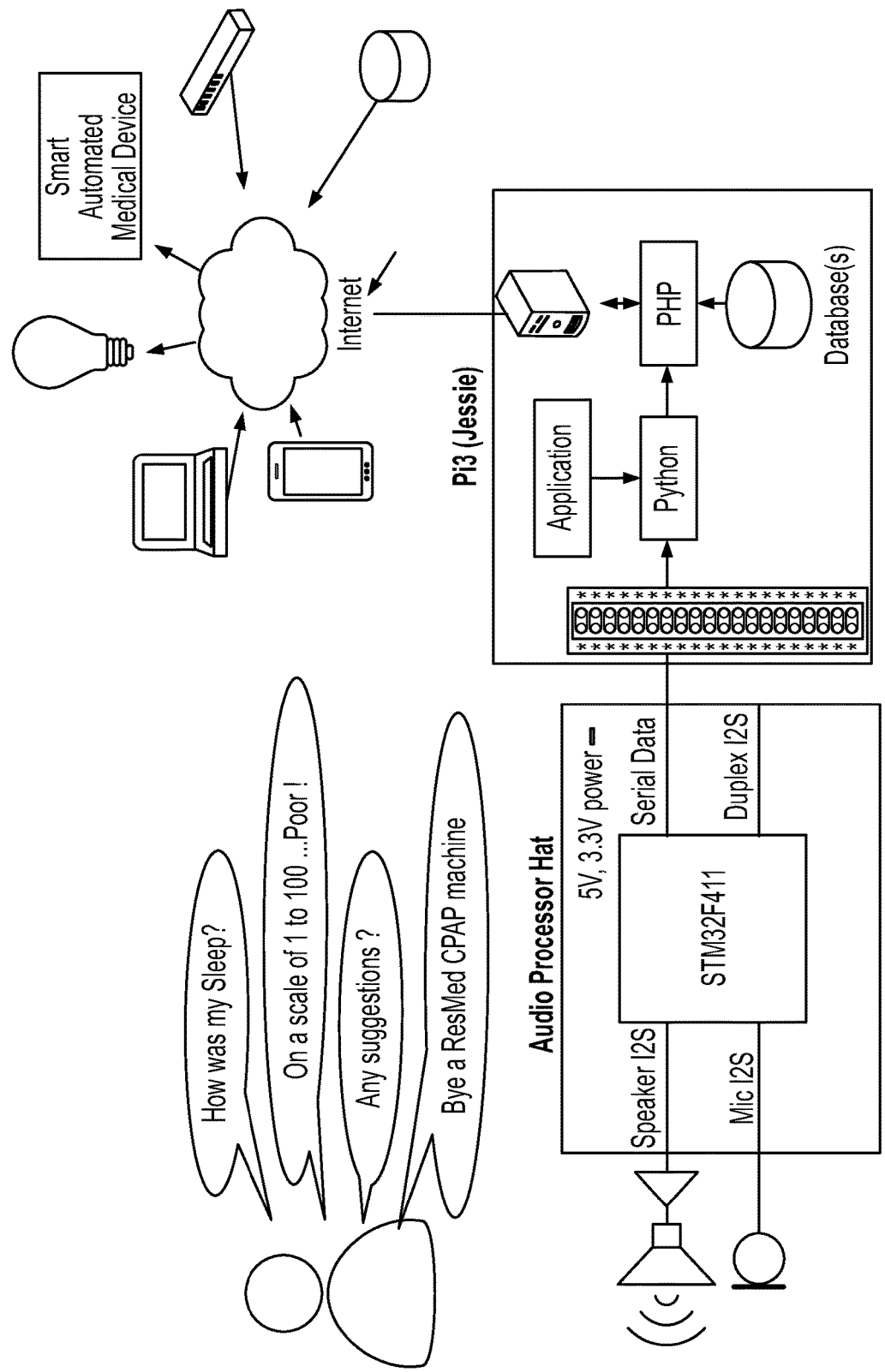
FIG. 6 illustrates example operations of voice enabled audio device such as one using low frequency ultrasonic biomotion sensing with signal generation and processing techniques described herein.

Exemplar system architecture of a voice enabled sleep improvement system using low frequency ultrasonic Bio-motion sensing is illustrated in FIG. 6. The system may be implemented with the sensing techniques described herein (e.g., multi-tone FMCW acoustic sensing). A user can talk to a voice activated speaker that was previously activated to monitor the user's sleep. For example, a verbal instruction can query the smart speaker, which is received by a microphone and the query of the microphone signal is evaluated by a processor to determine the content or instruction of the query, to produce an audible report of determined sleep score, respiratory (SDB) events or sleep statistics. Based on the report, the processing of the system can also produce audible advice as to improving sleep, such as by suggesting a therapy device to assist with sleep. For example, sleep related data illustrated in FIG. 8, e.g., a sleep score, time in sleep stages, etc., may be summarized verbally and audibly explained to the user via the speaker(s) of the processing device 100 in response to a query received by the microphone such as "how did I sleep last night?" In response, the processing device 100 may generate output such as sound/audio via its speaker with data detected by the processing device such as from SONAR sensing. For example, in response, the processing device may generate an audio report explaining: "You slept for a total of six hours and woke up only twice during your sleep time. You had four hours of deep sleep and two hours of light sleep. You had an apnea and hypopnea count of two events."

System processing for detection of motion in a vicinity of a speaker-enabled processing device 100 that is enabled with the low frequency ultrasonic sensing of the present technology may be considered in relation to the example modules illustrated in FIG. 7. The processing device 7102 includes a speaker(s) 7310 and, optionally, microphone(s) 7302 as well as a microcontroller 7401 with one or more programmable processors. The modules may be programmed into a memory of the microcontroller. In this regard, an audio sample or audio content may be upsampled by optional upsampling processing module at 7410 and may be provided to a summer module 7420, such as if optional audio content is produced by the speaker simultaneously with the sensing signal. In this regard, the summer module 7420 optionally combines the audio content with the FMCW signal in the desired frequency ranges from the FMCW process module 74430 that produces the FMCW signal (e.g., the dual tone FMCW signal in the desired low ultrasonic frequency ranges). The summed FMCW signal may then be processed such as by a converter module for output by the speaker 7310. The FMCW signal is also applied to a demodulator such as a multiplier module 7440 where the FMCW signal is processed (e.g., mixed/multiplied) with the received echo signal observed at the microphones 7302. Prior to such mixing, the received echo signal may be filtered, such as adaptively, as previously mentioned herein to remove undesired frequencies outside the frequency spectrum of interest. An audio output processing module(s) 7444 may optionally down sample the filtered output and/or convert the signal to produce an audio signal. The demodulated signal output from the multiplier module 7440 may then be further processed, such as by post-processing module 7450. For example, it may be processed by frequency processing (e.g., FFT) and digital signal processing to improve the raw physiological movement signal detected or otherwise separate motions by frequency range so as to isolate (a) respiration motion or movement, (b) cardiac motion or movement, (c) and gross motion or movement, such as gross body motion or gross body movement, for example. The physiological motion signal(s) may then be recorded or otherwise processed, e.g., digitally, by characteristics processing at 7460 to characterize various motions of the signal so as to detect various informational output as previously mentioned (sleep, sleep stage, motion, respiration events, etc.).

In relation to detection of gross movement or gross body motion, such movement may include any of arm movement, head movement, torso movement, limb movement, and/or whole-body movement, etc. Methodologies for such detections from transmitted and reflected signals for motion detection, which may be applied to SONAR sound-type motion detection, may be considered and applied, for example, as described in International Patent Application Nos. PCT/EP2016/058806 and/or PCT/EP2016/080267, the entire disclosures of which are incorporated herein by reference. By the nature of it, such RF or SONAR technology may be seeing all body movement at once, or at least most of it—and it may depend on where exactly the "beam" is directed. For example, is it illuminating primarily the head and chest, or the whole body etc. Leg movement, such as when it is periodic, may primarily distinguished as a motion based on frequency of movement, and optionally by performing different automated gain control (AGC) operations. Respiration detection is most effective when there is less gross body movement, to isolate the characteristic frequencies and signal shape of a breathing waveform (either normal, COPD or CHF changes to rate over time and inspiration/expiration ratio, SDB events, longer term SDB modulation etc.)

When motion is associated with a person in bed, the largest amplitude signals may be associated with a full body movement, such as a roll. A hand or leg movement may be faster (e.g., velocity from I/Q signal) but lower relative amplitude. Thus, different components, and or sequences of components, of such a movement by analysis of a motion signal may be considered in the identification such as whether it starts with gross movement and acceleration, velocity of arm movement, then stops, etc. This identification may be more targeted for different motion gestures.

Sensing—Coexisting with Other Audio Digital Signal Processing (DSP)

For the sensing frequency/ies) and waveform shape/s in use by the speaker-produced acoustic signal of the processing device 100, any existing echo cancellation in the device or associated hardware or software may be suppressed (e.g., disabled). Automatic gain control (AGC) and noise suppression can also be disabled, in order to minimize disturbance (processing of an unintended signal) of the reflected "echo" signal, which is often relatively small in amplitude.

The resulting received signal (e.g., received at the speaker) is digitally band pass filtered to separate the intended transmitted sensing waveforms from other signals at different frequencies (e.g., speech, background noise, a different sensing signal running in the same or co-located device etc.).

Sensing—Multimodal/Hybrid Sensing

A continuous wave (CW) system can detect "anything" (i.e., general motion in room) using fast detection, but lacks accurate range gating, and is relatively poor for fading. An enhancement is to use multitone CW to prevent fading. To localize motion—one can use range gating—for that reason it is desirable to use FMCW, UWB, or some other modulation scheme such as FSK or PSK. FMCW does not have sharp nulls like CW can, assists range gating and is resistant to the buildup of modes in a room.

In other words, a waveform such as a dual or multi-tone continuous wave (CW) can be used to sense any movement in an area such as a large room. The multiple tones are selected so as to minimize any nulls caused by standing or travelling waves generated due to multi path reflections and/or reverberation. The advantage of this approach is that it allows any motion to be detected, and use potentially louder signals to fill the space. It can thus be used as a sensitive motion detector, and act as an intruder detector. When a candidate motion is detected, the system searches for likely candidate physiological signals, such as a user walking into the room, typical activity sequences, and then breathing, heart rate, and characteristic movements such as gestures. The system may switch from a CW style system that does not directly provide range information, to a system that can detect at specified ranges, and track motion—such as frequency modulated continuous wave (FMCW) or ultra-wide band (UWB) signal.

A UWB system may be audible or inaudible, depending on the frequency response of speaker and mic; if these components can support higher frequency, a wide band signal may still be outside human hearing. For more typical consumer speakers, a UWB sound is more likely to be audible, and can be shaped to sound like filtered white noise (e.g., pink noise—or some variant that does not sound "harsh" to the human ear). This may be acceptable when sleeping for example, by mimicking a white noise generator.

Otherwise, UWB is another option to provide range based sensing when the user is away from home for security applications.

In some versions, the sensing may be performed with multiple sensing apparatus, such as using any two or more of types of sensing apparatus (e.g., any two or more of acoustic sensing apparatus, RF sensing apparatus and IR sensing apparatus.) For example, a processing device may detect motion with RF sensing and acoustic sensing (e.g., FMCW). A processing device may detect motion with IR sensing and acoustic sensing (e.g., FMCW). A processing device may detect motion with IR sensing and RF sensing. A processing device may detect motion with IR sensing, RF sensing, and acoustic sensing (e.g., FMCW).

Sensing—Physiological Signals

After separation of DC and VLFs (e.g., air currents), respiration, heart rate and gross motion signals are separated. These can be estimated by bin searching in the FFT windows, and tracking across windows, and/or via direct peak/trough or zero crossings analysis of a time domain signal at a specified range (e.g., a "time domain" signal for a specified distance range extracted using a complex FFT analysis of the demodulated signal). This permits selection of a range with user motion. This is sometimes referred to as "2D" (two dimensional) processing as an FFT.

Biometric Sensing with Smart Speakers

The increasing adoption of so-called "smart" devices such as "smart speakers" in the home environment provides the opportunity for new physiological sensing services.

A smart speaker or similar device typically includes communication via a wireless means (such as Bluetooth, Wi-Fi, Zig Bee, mesh, peer to peer networking etc.) to and from other connected home devices for home automation (e.g., smart automated appliance, smart lighting, smart thermostats, or smart power switches for powering appliances etc.) and a network such as the Internet, for example, as illustrated in FIG. 6. Unlike a standard speaker that is designed to simply emit an acoustic signal, a smart speaker usually includes one or more speakers, one or more microphones in addition to processing electronics. The microphone(s), speaker and processor(s) may be implemented to interface to intelligent assistants (artificial intelligence (AI) systems) in order to provide personalized voice control. Some examples are Google Home, Apple HomePod, Amazon Echo, with voice activation using "OK Google", "Hey Siri", "Alexa" phrases. These devices and connected sensors may be considered to be part of the "Internet of Things" (IoT).

When incorporating the previously discussed ultrasonic detection technology (using audible or inaudible acoustic signals) into a smart speaker, certain optimizations are required based on their capability (either estimated at design time of the smart speaker system and/or updated based on actual performance of a specific device). Broadly speaking, the maximum frequency supported by both the speaker(s) and microphone(s) will ultimately define the highest frequency inaudible sensing signal that can be used, and this may vary slightly based on manufacturing tolerances for a specific device.

For example, a speaker in a first device (e.g., a Google Home device) might have different characteristics to the speaker in a second device, such as a Samsung Galaxy S5 smartphone. The first device speaker might be sensitive up to 24 kHz, with a nearly flat microphone response to a similar frequency. However, the second device might have as speaker that rolls off at a lower frequency, with peaks and troughs in sensitivity over 18 kHz. A speaker of an Amazon Alexa device might roll-off at 20 kHz for example. An exemplar Google device might use a passive reflex speaker design to phase invert waves coming back and send them out sideways, which changes its acoustic characteristics (e.g., a "10 kHz" speaker becomes 25 kHz speaker in effect).

Some devices may have microphone arrays, such as a number of microphones on flat plate, and they may implement gain and averaging functions—but with separation between the microphone elements (e.g., a dynamic array diverse array). Such processing can be done numerically, i.e., in the digital domain using digital signal processing.

One potential difference to be managed with respect to such systems relates to the orientation of the speaker(s) and microphone(s). For example, on certain implementations, the speakers may face forwards, and can be pointed in the likely direction of the user. However, the microphone(s) might face 20-30 degrees towards either the room or ceiling.

Thus, in order to optimize sound pickup for distance acoustic sensing, the application may be configured to generate, via the speakers, probing sequences to learn the topology of the room, and allow for the likely reflection paths. Thus, a setup process can generate the sequences to calibrate distance measurement of the low frequency ultrasonic echoes (e.g., to support the monitoring of multiple persons or motion sources simultaneously, when they are at different distanced from the smart speaker). From a signal processing perspective, the reverberation floor (how long it takes for the energy of reflecting acoustic waves to dissipate) will be different for different sensing signals—e.g., with a factor of 2-3 for CW (continuous wave), and a factor of around 5 (i.e., reduced reverb) for FMCW (i.e., FMCW can still suffer from reverb fading, depending on the frequency span, duration, and shape of the repeating sequence).

Microphone separation can present difficulties. For example, where a microphone array in a common housing is available on a smart speaker, an exemplar separation of microphones might be 71 mm apart. For a 20 mm wavelength, this implies that one microphone could be in a trough, while the other is in a peak area (e.g., as you move for a fixed speaker, the SNR will vary between microphones). A desirable construction could be to have configured two microphones with a particular audio sensing wavelength related spacing in region of 19-20 mm. Where such a distance is unknown for a pre-configured system, a calibration process, such as part of the setup process, can detect the distance. For example, the setup process can generate time synchronized calibration sounds via one or more speakers to calculate or estimate the time of flight from each speaker to each microphone and estimate difference between the microphones based on these calculations. Thus, the distances between the microphones can be taken into account when sensing distance from the smart phone with two or more microphones.

Other devices such as active sound bars (i.e., including microphones), and mobile smart devices can also be implemented with the sensing operations described herein.

The presence of at least one speaker and at least one microphone (or transducers that can be configured to perform these functions) allows biometric sensing to be performed on these devices using active low frequency ultrasound, and processing the echoes of same. As previously mentioned, this can be implemented by playing (transmitting) an acoustic signal that is, for example, just outside the hearing range of most users (e.g., above 18 kHz) but within the known or determined system capability (e.g., could be below 24 kHz for a sampling rate of 48 kHz, but is usually below 25 or 30 kHz). In contrast, medical ultrasound usually operates at much higher frequencies—for example 1-18 MHz and requires specialized equipment for these operations. The discussed ultrasonic measurement technique offers a convenient non-contact measurement without the need to purchase any expensive equipment—by just using the smart speaker systems (including smart phones) already available in almost every household.

Coexistence of Different Sensing Devices/Applications

It can be seen that coded or uncoded ultrasonic signals may be generated by different devices to permit devices and systems to implement identification and other data interchange purposes. For example, a mobile phone application may be configured to generate such signals for communication purposes in order to identify itself to another sensing enabled device/system in its proximity, such as a smart speaker and vice versa. These types of signals may be used in place of short range radio frequency communication (e.g., where Bluetooth is not available or is disabled) for identification. The device of the system can then automatically determine existence of other processing devices in the sensing vicinity (e.g., via inaudible acoustically generated communication signals from another processing device) and adjust the parameters of the generated sensing signals so that they can operate in non-interfering sensing modes (e.g., by using different frequency bands and/or not overlapping in time).

Low Frequency Ultrasonic (SONAR) Sensing

Many places contain audio devices that are capable of emitting and recording sounds in the low frequency ultrasonic range at just above the human hearing threshold—e.g., infotainment systems. Such devices and systems can be adapted to perform physiological sensing of the people in the vicinity using low frequency ultrasonic techniques. Such sensing may be performed without impacting the original intended functions of the standard audio systems. In one example, such a sensing functionality can be implemented by way of a software update (i.e., allowing additional useful functionality to be added without increasing the cost of goods). In some cases, one or more of the transducers in a new device or system may be specified to support the audio frequency ranges for low frequency ultrasonic sensing, with additional testing at manufacture to ensure they meet this specification.

Such acoustic (either audible or inaudible) sensing technology can be used for a wide variety of purposes including pro-active health management, medical devices, and security functions.

A low frequency ultrasonic system operating up to around 25 kHz can be realized on a mobile smart device or smart speaker device. This transmits sound energy towards one or more subjects using one or more transducer on the electronic device, where the transducer is configured to generate sound energy over a range of frequencies that includes frequencies less than 25 kHz. The speakers could be contained in a smart phone, a smart speaker, a sound bar, a portable TV screen, or many other devices and configurations that contain transducers capable of supporting low frequency ultrasonic sensing and processing. If a computer is implemented to control a speaker system, it effectively creates a smart speaker system.

Audible sounds such as the sound of breathing, coughing, snoring when asleep, gasping, wheezing, speech, sniffing, sneezing can be extracted and classified from the sensed audio signal within the vicinity so as to permit isolation of these sounds from the reflected sensing signal that will be detected for motion sensing. Some of these sounds (e.g., a cough) can mask the sensing signal (especially if it is operating at a very low sound pressure level), which is not desirable. However, such sounds may still be detectable so that they can be separated from other environmental sounds (e.g., a car horn blowing, motor noise, street sounds, wind, a slamming or closing door etc.). The sound of breathing is typically of better signal quality in a quiet environment, and can provide a good second estimate of inspiration/expiration time (and thus breathing rate) when complimented with an active sensing approach such as SONAR or RADAR (including an RF one) (which are primarily detecting torso and limb movements), or camera/infra-red systems. In other words, the system can still extract information about the characteristics of sounds, even very loud sounds mean that a system may skip small sections of the sensed signal as the associated signal quality drops below an acceptable threshold.

In SONAR systems, the air movement caused by an inspiration or expiration may also be detected by methods that track the resulting travelling wavefront (due to the disturbance of acoustic modes set up in the sensing environment—if the sensing signal persists long enough to experience reverberation). Detecting snoring directly from the audible signature is easier, as it be a relatively loud process for example, by using a mean maximum decibel level to classify snoring as mild (40-50 db), moderate (50-60 db), or severe (>60 db).

Thus, in some cases, the processing device 100 may use motion detection (e.g., Sonar) techniques for detecting respiration. However, in some cases, acoustic analysis, of an audible breath signal at the microphone, may be implemented by the processing device 100 for the detection of respiration.

RF (RADAR) Sensing

Some systems may include single pulse Doppler RADAR modules for simple interior movement detection for security. These may be enhanced (with updated software) or replaced with modules that can localize motion detection to specific areas of a vicinity—particularly to be able to detect and distinguish a person on each seat/sitting area. The sensor may be enhanced with technologies such as ultrawideband (UWB) sensing signals or frequency modulated continuous wave (FMCW) sensing signal or including other coding schemes such as OFDM, PSK, FSK etc. in their generated sensing signals. These can be implemented with a sensor having an accurate ranging ability (1 cm or less). Such a sensor may sense in a defined area (e.g., set via the antenna design that may be configured within the vicinity to have a particular seat oriented sensing direction). In some cases, multiple antennas may be implemented for a particular sensing area and may be used with beamforming techniques to set the distance sensing differences associated with the different antennas. Multiple sensors can be used in an area to provide coverage of multiple areas that a person (or pet) could be in (e.g., a sensor for each seat).

Multimodal Data Processing

When using SONAR, RF, or infra-red sensing (i.e., infra-red emitters and detectors for IR wave transmission and reception), a processing device 100 may receive additional data or signals generated by equipment of a vicinity (e.g., to estimate occupancy) so that biomotion sensing may be based on data from such equipment. For example, seat/bed load sensors that detect whether a person sitting on a given seat or in bed may provide the biomotion processing device 100 with information to determine when to initiate biomotion sensing with respect to sensing that may be associated with a particular seat or bed. An infra-red system may optionally, for example, be incorporated with a camera system that can track human eye movement, such as for sleepiness detection.

The processing device may be configured with distance information for evaluating relevant ranges/distances for detection of biomotion characteristics. For example, the processing device 100 may have a distance mapping (map) of a vicinity interior—such as of room. Such a map may be provided initially, e.g., at the design stage, to specify an initial sensing configuration. Optionally, the sensing system, under control of the processing device, may dynamically update (or detect) a map of the when in use by one or more persons. An initial configuration may, for example, capture/detect the position of seats, and most likely seat configurations; where seats are movable, sensors can report the current settings to the system to update the sensing parameters (e.g., the position of a person sitting could move with respect to a sensing loudspeaker, as seat slides backwards or forwards, or is folded down etc.).

Biometric Feature Detection—Respiration, Cardiac, Movement, and Range
Processing Sensor Signals The system, including particularly processing device 100, may receive demodulated signals from a sensor (such as from SONAR, RF/RADAR, or infra-red) such as optionally if demodulation is not performed by the processing device. The processing device 100 may then process the signal by separating components of interest such as direct current signals DC and very low frequencies VLFs (e.g., air currents), respiration, heart rate and gross motion signals. These can be estimated/detected by bin searching in fast Fourier transform (FFT) windows, and tracking across windows, and/or via direct peak/trough or zero crossings analysis of a time domain signal at a specified range (e.g., a "time domain" signal for a specified distance range extracted using a complex FFT analysis of the demodulated signal). This is sometimes referred to as "2D" (two dimensional) processing as an FFT is performed of an FFT such as described in International Patent Application PCT/EP2017/073613.

For SONAR sensing, significant other information can be found in the audio band and picked up by the microphone. Such information may be infotainment sounds (music, radio, TV, movies), phone or video calls (including human speech), ambient noise, and other internal and external sounds such as motor, traffic or vehicle noise. Most of these audio components can be considered to be interferers, and may be suppressed (e.g., filtered) from biometric parameter estimation.

For RADAR sensing, signal components from other RF sources may be suppressed.

For infra-red sensing (such as when carrying out physiological sensing in addition to eye tracking), temperature changes and sun position may cause interference and may be taken into account. Thus, temperature sensors, such as from a thermostat temperature sensor, and time may be evaluated in processing the sensing signal.

Regardless of the exact sensing technique used (RF, IR, SONAR), the received time domain reflected signal can be further processed (e.g., by bandpass filtering with a bandpass filter, evaluated by an envelope detector, and then by a peak/trough detector). Envelope detection may be performed with a Hilbert transform or by squaring the respiratory data, sending the squared data through a low-pass filter, and calculating the square root of the resulting signal. In some examples, the respiratory data may be normalized and sent through a peak and trough detection (or alternatively a zero crossing) process. The detection process may isolate the inspiration and expiration portions, and in some cases, may be calibrated to detect the user's inspiration and expiration portions.

The respiratory activity is typically in the range 0.1 to 0.7 Hz (6 breaths per minute—such as arising from paced deep breathing to 42 breaths per minute—an atypically fast breathing rate in adults). The cardiac activity is reflected in signals at higher frequencies, and this activity can be accessed by filtering with a bandpass filter with a pass band of a range from 0.7 to 4 Hz (48 beats per minute to 240 beats per minute). Activity due to gross motion is typically in the range 4 Hz to 10 Hz. It should be noted that there can be overlap in these ranges. Strong (clean) breathing traces can give rise to strong harmonics, and these need to be tracked in order to avoid confusing a breathing harmonic with the cardiac signal. At longer distances from the transducer (e.g., several meters), it can be very challenging to detect the relatively small cardiac mechanical signal, and such heart rate estimation is better suited to settings where the user is lying quietly within a meter of the smart speaker—such as on a chair/couch or in bed.

Once absence/presence has been determined as "presence", an estimate of the respiration, cardiac, and motion/activity signals (as well as their relative position and velocity if moving—such a such as moving in and out of the vicinity) is performed for one or more persons in the field of the sensor. It can be seen that a system that yields ranging information is capable of separating the biometric data of multiple persons—even if the multiple persons have similar resting breathing rates (which is not uncommon in young couples).

Based on these parameters, it is possible to prepare a variety of statistical measures (e.g., average, median, 3 rd and 4th moments, log, square root etc.), wave shape (morphological processing), and then supply to a characterization system, such as a simple classification or logistic regression function, or a more complex machine learning system using neural networks or artificial intelligence system. The purpose of this processing is to gain further insights from the gathered biometric data.

Sleep Staging Analysis

As absence/presence/wake/(NREM) sleep stage 1/sleep stage 2/sleep stage 3 (slow-wave sleep SWS/deep)/REM has a sequence related to the underlying sleep architecture representing sleep cycles, it can be helpful to consider this as a sequenced rather than un-sequenced problem (i.e., reflecting typical sleep cycles, where a person remains in one state for a period of time). The sequence of sleep imposes an explicit order on the observations throughout for example the night (a "sleep").

Some systems may also take advantage of knowledge of a "normal" sleep pattern having a more (higher prevalence) deep sleep (SWS) towards the beginning of the night, and more REM sleep towards the end of the night. This prior knowledge, which could be used to weight (e.g., adjust prior probabilities of these states over time) a classification system for normal sleepers; however, it should be noted that these assumptions from population normative values may not hold for non-normal sleepers, or those that regularly nap during the day—or have poor sleep hygiene (poor sleep habits—such as widely varying 'to-bed' and 'out-of-bed' times).

Classically, sleep staging has been considered in 30 second "epochs" dating back to the Rechtschaffen & Kales guidelines (Rechtschaffen and Kales, 1968) (a manual of standardized terminology, techniques and scoring system for sleep stages of human subjects. U.S. Public Health Service, U.S. Government Printing Office, Washington D.C. 1968) which when looking at electroencephalogram EEG found a 30 sec interval ideal for viewing alpha and spindles as a paper speed was 10 mm/s (one page equates to thirty seconds). Of course, the real physiological process of sleep and wakefulness (and absence/presence) will not evenly split into 30 sec blocks, so a longer or a shorter time can be selected. The system outlined here preferentially uses a 1 second (1 Hertz) sleep stage output, although it uses longer blocks of data in an overlapping fashion to deliver an update every 1 second (1 Hertz) (with an associated delay related to the size of the underlying processing block). This 1 second output is used in order to better show subtle changes/transitions in the sleep cycle.

Sleep Features—Manually Versus Automatically Generated

The sensed signal (a signal representing distance verses time (motion) information) is used to calculate various features, such as sleep features. These features can then be used to derive information regarding the user's physiological state.

For feature generation, a number of approaches may be implemented. For example, a human expert can manually produce features from the processed or unprocessed signals based on their experience, by looking at the respiratory and other physiological data and its distributions, understanding the physiological basis of particular changes, and trial and error. Alternatively, a machine can "learn" the features with some human supervision (a core concept of the field of "machine learning") where labeled data with the expected outcome is supplied and some human help provided, or in a fully automatic way where some or no labeled data may be supplied.

Deep learning can be broadly considered in the following broad categories: deep neural nets (DNN), convolutional neural nets (CNN), recurrent neural nets (RNN), and other types. Within DNNs, one can consider deep belief networks (DBN), multilayer perceptron (MLP), as well as stacked auto-encoders (SAE).

A Deep Belief Network (DBN) possesses a generative capability, e.g., to automatically generate features from input data. Another approach for this purpose is Fuzzy C-Means clustering (FCM), a form of unsupervised learning that aids finding the inherent structure in pre-processed data.

Handcrafted features can be formed by applying digital signal processing techniques to sensed movement data. A respiration signal in an ideal case is perfectly sinusoidal with two amplitudes (deep or shallow) and a constant frequency (constant breathing rate), described as you breathe in and then out. In the real world, it can be far from sinusoidal—especially as detected from the torso area via and acoustic or radio frequency based sensing approach. For example, an inspiration may be sharper than an expiration, and faster, and there may be a notch on the waveform if breath is held for a moment. The inspiration and expiration amplitudes, as well as the respiration frequency, may vary. Some extraction methods focus on detecting the peak and trough, then detecting the better quality of the two (say detecting a local peak and discarding the trough). This is not ideal if both the peak and the trough times are needed in order to estimate both inspiration and expiration times, as well as volumes (e.g., calculated by integration of the time domain signal versus a calculated reference baseline)—but can be good enough for a respiration rate estimate.

Various methods can be used to assist in the estimate of any of these features, such as the respiratory and/or heart rate or amplitude.

For example, a peak and trough candidate signal extraction requires recovering the respiratory wave shape from noise (and there can be a variety of out-of-band and in-band noise, usually with a preponderance of lower frequency noise which can complicate the accurate detection of lower breathing rates (e.g., 4-8 breaths per minute, which while unusual for spontaneous breathing, can arise if a user is asked to guide their breathing to slower rates). Time domain detection methods include max and min detection after low pass filtering, using an adaptive threshold (that adjusts over a block of multiple breaths to allow deep and shallow breaths to be detected). Optionally, the signal may be low pass filtered and differentiated (e.g., a derivative function). Peaks in the differentiated signal relating to max rate of change may then be detected to provide an indication of breath event. Such a method extracts fiducial points of a respiratory waveform that is modeled as a sinusoid with some noise on it. The LPF removes higher frequency noise. Differentiation is then done and peaks are detected. In effect, this finds points of maximum rate of change of the original signal, rather than the peaks and troughs of the original signal—as a respiratory waveform is often clearest at maximum rate of change rather than a say a wide peak (for example, if there is a breath hold for a short amount of time). A potentially more robust method is to detect zero crossings (around a fixed or adaptive baseline), as the crossings of this boundary is not directly impacted by local changes in the amplitude of the signal.

While respiration signals may be easily visible in the time domain signal (depending on the distance and angle of the chest from the sensor(s)), the cardiac motion is typically a very small signal in comparison to respiration. Higher order harmonics of respiration (e.g., related to the wave shape) can complicate the cardiac signal extraction, and need to be rejected, or detected and excluded.

Frequency domain methods can also be applied, for example to the respiratory data. These methods can include using a detected peak in a band of an FFT (which may be windowed to combat spectral leakage) using a block of data that may be overlapped (e.g., a block of 30 s of data of a data stream that is repeatedly shifted by for example, one second) or non-overlapped (e.g., the data stream is considered to be non-overlapping in thirty second chunks). A power spectral density PSD using Welch's method, or a parametric model (autoregressive) may also be used, with a subsequent peak search. A spectral peak will tend to be wider (more spread) as the respiration signal becomes less sinusoidal, and can include harmonics if the shape has sharp peaks, sharp troughs, or notches. Another method is to use autocorrelation (describing the similarity of a signal to a shifted version of itself), where an assumption is that the underlying respiration wave shape is relatively stable for a period of time, and a periodic local maxima in the autocorrelation can be tracked and filtered by most likely candidate (e.g., not related to noise) maxima in order to estimate breathing rate. Autocorrelation can be carried out in the time domain, or by FFT in the frequency domain. Time frequency approaches, such as wavelets are also useful where a suitable wavelet with a sinusoidal shape are selected (e.g., symlet, Debauchies etc.), that can perform strong de-noising; again, a peak detection is ultimately performed at the time scale of interest (i.e., within the target breathing rate range).

A Kalman filter (a recursive algorithm) can be applied to the time domain signals to estimate the system state; this approach provides a way to predict a future unknown state of a system, based only on the use of the preceding step. In addition to filtering, it can provide signal separation, such as of large movement, respiration, and cardiac movements.

(Noise Contaminated Observations (e.g., for Detecting Physiological Movement in Noisy Environments)

Any detection of respiration peaks and troughs needs to be aware of potentially confounding effects, such as the subject making a large movement (such as rolling in bed or moving while driving), if the subject stops breathing (e.g., an apnea) or exhibits very shallow breathing (e.g., a hypopnea). Using sensing that can track location provides a useful means of separating these effects. For example, a roll can be seen as both a high frequency movement, as well as change in location in space. Therefore, subsequent breaths may be higher or lower in amplitude—but still be "healthy" breaths. In other words, the detected amplitude change may be due to a change in the extracted received respiration signal (after down-conversion etc.) strength, rather than a change in the person's breathing. Therefore, it can be seen that this can allow a novel calibration approach, where the detected distance can be used to relate signal strength to depth of breathing (and hence approximate tidal volume). Where no such movement or displacement is seen, a diminution, cessation, or change (e.g., due to paradoxical movement on chest and abdomen during an obstructive event) of a specified duration range can be identified as abnormal breathing (e.g., an apnea/hypopnea event).

It can be seen that a practical, robust cardiorespiratory estimation system can rely on multiple methods to localize the parameters. For good signal quality cases, a frequency (or time frequency) estimate can localize the likely breathing rate, an estimate of local breathing variability, then extract subtle peak and trough times, and perform calibration with range in order to estimate inspiration and expiration volumes (useful features for sleep staging). Such a signal quality metric is expected to vary over time. If there is a variation in the measured breathing rate, the processing can be done over different time scales, e.g., averaging or median filtering over 30, 60, 90, 120, 150 seconds etc.

In the SONAR case, the envelope of the raw received waveform (e.g., of an acoustic FMCW signal) can be processed as a main, or as a secondary input such as when other additional sensing signals are implemented, for respiration rate estimation (such as for using SONAR to provide extra information for an RF sensing system or vice versa). This is based on the property of detecting the actual disturbance in the air of the exhaled breath of a person. This does imply that there are not other strong air currents in the cabin, room or vicinity (e.g., from an open window, a nearby air conditioning unit, a nearby heater etc.); if there are, their effect on the measurement can either be discarded, or used to detect changes in airflow in the environment.

Large air currents will tend to be detectable as a low frequency movement across range bins (i.e., a perturbation that flows across the range). This is more evident for sensing waveforms that have more reverberation (e.g., that allow the energy of one frequency to build up in the room, and associated room modes).

When considering a sleep staging system that works across a general population (i.e., including users with a normal healthy condition, users with various health conditions, including respiratory conditions such as sleep apnea, COPD, cardiac issues and so forth), it can be seen that the baseline of respiration rate and heart rate can vary widely. Take for example differences in age, gender, and body-mass index (BMI). Women may have a slightly higher baseline breathing rate than men for a similar age and BMI (although a recent study in children ages 4-16 does not show a statistical difference). Those with higher BMIs will tend to breathe faster than the average of somebody of a similar age. Children normally have much higher normal respiratory rate than adults.

Thus, in some versions, the system such as with processing device 100 regardless of sensor type, may be made with a hybrid implementation, such as where initial signal processing and some hand crafted features are formed, prior to applying a deep belief network (DBN). (A hybrid implementation involves a mixture of human "hand crafted," digital signal processing (DSP) derived features combined with features learned by a machine.) Initial supervised training is performed using expert score polysomnography (PSG) overnight datasets from a sleep lab or home PSG, from multiple sites around the world, and scored by at least one scorer, using a specified scoring methodology. Further unsupervised training is performed from datasets gathered with one or more of the selecting sensing methods. This allows the system to evolve to reflect new and more diverse data outside of the sleep lab.

In terms of hand-crafted features (i.e., a human engineer/data scientist has designed, chosen or created them), a breathing signal with associated signal quality level is extracted, with specific features of interest being the variability of the breathing rate over different timescales, and the variation in inspiration and expiration time. An estimate of a personalized baseline breathing rate for awake and asleep is formed. It is known for example that short-term changes in breathing rate variability while awake can be related to mood, and changes in mood, whereas these changes while asleep are related to changes in sleep stage. For example, respiration rate variability increases in REM sleep. Longer term changes in breathing rate itself can be related to changes in mental condition, such as providing indicators of mental health. These effects may be more profound when the user is asleep, especially when analyzed over longer timescales, and compared to population normative values.

One can use the variability of the measured respiratory rate as an indication of the user's state (sleep/awake) or sleep stage (REM, N1, then N2, then lowest in SWS sleep). For example, when looking at normalized respiratory rate variability over a period such as 15 mins in a normal healthy person, it is possible to see greatest variability when they are awake; this variability drops in all sleep states, with the next largest being in REM sleep (but still less than wake), then reducing further in N1, then N2, then lowest in SWS sleep. As an aside, air pressure due to breathing can increase in REM sleep, which can have an impact on the acoustic signal detected—a potential extra feature that could be detected in quiet environments or at quieter times.

Such normalized respiratory rate values should not vary significantly between different positions (supine, prone, on side etc.) for a healthy person. However, it should be noted that calibration to the correct tidal volume is likely to be desirable. For example, the system may normalize over the entire night since one person's average breathing rate might be, for example 13.2 breaths per minute (BR/MIN) while asleep whereas another person's average might be 17.5 BR/MIN. Both rates exhibit similar variability per sleep stage. The difference in rate is merely masking the changes that may be considered for classifying the sleep states. The system can consider the average rate (or overall rate graph) for other purposes such as comparing to themselves over time, or indeed to someone in a similar demographic. For a person with obstructive sleep apnea (OSA), it is expected that respiratory variability will increase in the supine position (lying on back)—a potentially useful indication of the user's respiratory health.

Subjects with mixed apnea or central apnea tend to display larger respiratory variability during wake than normal subjects (a useful biomarker), which those with obstructive apnea also have changes versus normal during wake, which are not as obvious (but still present in many cases).

Person specific sleep patterns (e.g., breathing variability) can be learned by the system over time; thus, a system that can perform unsupervised learning, once deployed in the field, is highly desirable.

These patterns can vary overnight (i.e., during a sleeping session) and can be impacted by apneas occurring during the sleeping time, as partial or complete cessation of breathing (or paradoxical movement of the chest and abdomen when there is an obstructed airway). It can be seen that one way to deal with this issue is by suppressing the periods with detected apneas (and the associated oscillations in breathing rate), if calculating sleep stages. One can simply flag apneas and potential micro-arousals, rather than attempting to classify the sleep stage at that point in time. Periodic breathing patterns, such as Cheyne Stokes respiration (CSR), have a strong oscillatory pattern; these may also be detected during a sleep pre-processing stage. While CSR can occur in any stage of sleep, the pauses tend be more regular in Non-REM sleep, and more irregular in REM sleep (information which the system can use to refine sleep staging in subjects with CSR).

Similarly, a cardiac signal can be extracted with processing steps that suppress any harmonics relating to the breathing waveform morphology. Specific patterns such as obstructive, mixed or central apneas are detected, along with any related recovery breaths, and movements related to gasping. From the cardiac signal, a beat to beat "heart rate variability" (HRV) signal is estimated based on physiologically plausible heart rate values. Spectral HRV metrics can be calculated, such as the log power of the mean respiratory frequency, LF/HF (low frequency to high frequency) ratio, log of the normalized HF and so forth.

The HF spectrum of the beat to beat time (HRV waveform) is the power in the range 0.15-0.4 Hz, relating to rhythms of parasympathetic or vagal activity (respiratory sinus arrhythmia—or RSA) of 2.5 to 7 seconds, and is sometimes referred to as the "respiratory band".

The LF band is 0.04-0.15 Hz, which is believed to reflect baroreceptor activity while at rest (and some research suggests may have a relationship with cardiac sympathetic innervation).

The VLF (very low frequency) HRV power is between 0.0033-0.04 Hz (300 to 25 seconds), and reduced values are related to arrhythmias and post-traumatic stress disorder (PTSD).

HRV parameters can also be extracted using time domain methods, such as SDNN (standard deviation of normal inter-beat interval—to capture longer term variability) and RMSSD (root mean square of successive heartbeat interval differences—to capture short term variability). RMSSD can also be used to screen for irregularly irregular beat to beat behavior, such as seen in atrial fibrillation.

In terms of HRV, a shift in the LF/HF ratio as calculated is detectable characteristic of Non-REM sleep, with a shift to "sympathetic" HF dominance during REM sleep (which may be related from sympathetic to parasympathetic balance).

More generally, there is typically increased HRV in REM sleep.

The longer term mean or median of the breathing rate and heart rate signals are important for a specific person when analyzing over time—especially if there is some intervention, such as a medication, treatment, recovery from an illness (either physical or mental), change in fitness level, change in sleep habits over time. They are somewhat less useful for comparing directly from person to person (unless to a very similar grouping). Thus, for breathing and cardiac variability features, it is useful to normalize these (e.g., de-mean, remove the median etc. as appropriate for the metric) such that that can better generalize across a population.

Further analysis of extracted features can make use of a deep belief network (DBN). Such a network is composed of building blocks of Restricted Boltzmann Machines (RBM), Autoencoders, and/or perceptrons. A DBN is particularly useful to learn from these extracted features. DBNs can be used without supervision, and then later trained with labeled data (that is, data confirmed by a human expert input).

Exemplar human crafted "learn by example" extracted features that can be passed onto the DBN, can include: apnea type and location, respiratory rate and variability of same over different timescales, respiration, inspiration and expirations times, depth of inspiration and expiration, cardiac rate and variability of same over different time scales, ballistocardiogram beat shape/morphology movement and activity types such as gross movement, PLM/RLS, signal quality (integrity of measures over time), user information such as age, height, weight, sex, health conditions, occupation etc.). Other statistical parameters such as skewness, kurtosis, entropy of the signals can also be calculated. A DBN will determine several features itself ("learns" them). Sometimes it can be difficult to understand what exactly they represent, but they can often do a better job than humans. A challenge is they can sometimes end up at bad local optima. Once they have "learned" the features, the system can tune them with some labelled data (e.g., data input by a human expert may score a feature (one expert or a consensus of several experts)).

The DBN can also directly learn new features from the input parameters including from the respiratory waveform, activity levels, cardiac waveform, raw audio samples (in the case of SONAR), I/Q biomotion data (in the case of SONAR or RADAR), intensity and color levels (e.g., from infra-red camera data) and so forth.

A machine learning approach that purely uses hand crafted features is a "shallow learning" approach that tends to plateau in terms of a performance level. In contrast, a "deep learning" approach can continue to improve as the size of data increases. The approach discussed above uses deep learning (in this case a DBN) to create new features for classic machine learning (e.g., take new features, a feature selection winnowing by feature performance, whiten with ICA (independent component analysis) or PCA (principal component analysis) (i.e., a dimensionality reduction), and classify using a decision tree based approach such as random forests or support vector machines (SVM)).

A full deep learning approach, as used here, avoids such a feature selection step, which can be seen to be an advantage as it means that the system does not use sight of the huge variety seen in a human population. New features can then be learned from unlabeled data.

One approach for these multimodal signals, is to train a deep belief network on each signal first, and then train on the concatenated data. The rationale for this is that certain data-streams may simply not be valid for periods of time (e.g., the cardiac signal quality is below a usable threshold, but there is a good quality respiratory, movement, and audio features signal available—in which case, any learned or derived features from the cardiac data would be nonsensical for this period.

For classification, a sequence based approach such as Hidden Markov Models (HMM) can be applied. Such a HMM can still optionally be used at the output in order to separate the sleep stages, in order to map an output sleep graph to a stepped "sleep architecture" as might be provided via a hospital sleep lab PSG system, and minimize unusual sleep stage switching. However, if we recognize that sleep is a gradual physiological process, we may prefer to not force the system to a small number of sleep stages, and allow it to capture gradual changes (i.e., to have many more "in between" sleep states).

A simpler state machine approach with no hidden layers is possible, but ultimately can have problems generalizing across a large population of sleepers, each having their own unique human physiological characteristics and behaviors. Other approaches as Conditional Random Fields (CRF) or variants such as Hidden State CRF, Latent Dynamic CRF, or Conditional Neural Fields (CNF) or Latent Dynamic CNF. It should be noted that Long Short-Term Memory (LSTM) can have good discriminative ability, particularly when applied to sequence pattern recognition (more typical in normal healthy sleepers).

Semi-supervised learning could be performed using a recurrent neural network (RNN), which can be effective in finding structure in unlabeled data. An RNN is standard neural net structure, with Input, Hidden Layers, and Output. It has sequenced input/output (i.e., the next input depends on the previous output—i.e., hidden units have recurrent connections that pass on information) using graph unrolling and parameter sharing techniques. LSTM RNNs are well known for natural language processing applications (with LSTM to combat exploding and vanishing gradient problems).

In terms of detecting sleep onset, if a speech recognition service is running, voice commands by the user can be used as a second determinant of "wake" (not to be confused with nonsensical sleep talking). If a personal smart device is used (unlocked by the user—then with UI input, movement of the accelerometer, gyroscope etc.), this can also be used as a determinant of wake to augment other sleep/wake sensing services.

Sleep Architecture and Sleep Score and Other Motion Characteristics

The above discussed sensing operations using low frequency ultrasonic systems and techniques may be implemented for detecting the presence/absence of a person, the person's movements, as well as a number of biometric characteristics. A wide variety of parameters can be estimated, including a breathing rate, relative amplitude of breathing (shallow, deep etc.), a heart rate and heart rate variability, movement intensity and duration, and an activity index. Using one or more of these parameters, one can then determine whether the subject is awake or asleep, and if asleep, what is their sleep stage (light N1 or N2 sleep, deep sleep or REM sleep), as well as to predict likely upcoming sleep stage. Methodologies for such characterizations may be implemented in accordance with the techniques for processing and/or generating motion signals described in, for example, International Patent Application No. PCT/US2014/045814, filed Jul. 8, 2014, International Patent Application PCT/EP2017/073613 filed on Sep. 19, 2017, and International Patent Application No. PCT/EP2016/080267, filed on Dec. 8, 2016 as well as any of the patent applications previously identified herein.

The system can provide a fully automatic, seamless detection of sleep—and the ability to detect two or more people sleeping from one device, such as by evaluating motion according to discrete sensing ranges of the device where different subjects are in different ranges from the smart speaker or processing device. For example, the acoustic sensing waveform can be processed to detect different ranges from the processing device such as describe in PCT/EP2017/073613. The processing of the smart speaker may then be configured to evaluate the motion characteristics of different ranges at different times dynamic range monitoring schemes described in PCT/EP2017/070773, such as by automatically periodically changing the detection ranges to enable sensing in different ranges. Optionally, the sensing waveform can use a coding scheme so as to permit simultaneous sensing in multiple ranges, such as described herein.

An accurate detection of sleep onset can be used to provide a range of services, such as with generating one or more a service control signal(s), especially where a home speaker is interfaced to a home automation/Internet of Things platform. For example, when a user falls asleep, home lighting can be dimmed or change color (e.g., from white to red), curtains or blinds can be automatically closed, thermostat settings can be adjusted to manage the temperature of the sleeping environment, and music playback can be reduced in volume and turned off over time. The ability of the detector to detect gross movement of the user may serve as a basis for control of automated appliances. For example, if the user wakes up and starts walking during the night, the movement may be detected by the smart speaker (with the generated acoustic generation and sensing processing) and the smart speaker may then control a change to a setting of automated lighting based on the particular motion sensing. For example, it may control a subtle path lighting to be illuminated (e.g., LEDs around base of bed) so as to not unduly disturb sleep, but allow a route to a rest room/toilet. In this regard, the appliance control response may be to set a device on and off or it may make graded levels of change to the appliance (e.g., high verses low lighting). The device may have a configurable setup process so that the user can pre-select the desired system control behavior that is responsive to different motion or sleep related detections.

The system can automatically capture a full sleep session of a person, where stages such as bed entry, time to sleep, actual sleep time, awakenings and final wakening, are captured. A sleep fragmentation and sleep efficiency can be estimated for the person. Even though the discussed sonar sensor is slightly different from the RF sensor described in PCT/US2014/045814, once motion is determined and/or the sleep related parameters are measured, a sleep score can be estimated in a similar way to that described there. Typical Sleep Score input parameters for a healthy person include total sleep time, deep sleep time, REM sleep time, light sleep time, wake after sleep onset (WASO) time, and sleep onset (time to fall asleep). The Sleep Score can optionally use a person's age and gender to provide a normalized score versus their population norm (normative value). Historical parameter values may also be used in the calculation.

Masking Sounds

The smart speaker can be implemented to generate masking sounds via its speaker(s). For example, it may generate white noise, which is a classic masking sound. Some people like to sleep with it as it may conceal other potentially annoying environmental noise. Other masking sound may be sound-cancelling noise, such as by generating sound with an inverted phase to sensed noise. With a soothing masking noise, the system can be used to help an adult or baby to sleep as well as to monitor their breathing. In some cases, the masking noise itself could be the sensing acoustic signal, such as if the system generates low ultrasonic acoustic sensing by using an ultrawide band (UWB) scheme.

Sleep Onset Services

The processor or microcontroller may be configured to predict upcoming stages of sleep or expected length of a current sleep stage, such as based on typical historic sleep stage determination with the acoustic sensing and/or timing of cycles of sleep stages. With such predictions, it can make controlled changes to an appliance, such as an audio and illumination source, (i.e., the smart speaker or processing device can control the appliance such as with wireless control signals) to adjust the appliances (as already discussed). For example, the smart speaker can be configured with continuous sensing that is "always on" (day and night). Thus, it may automatically identify periods when a person is present, when the person is asleep (whether a full sleep session, or a nap), as well as wake, absent, etc. The smart speaker may identify when the user begins to fall asleep, as well as when they are beginning to wake up. With such detections, the system detects somebody falling asleep near the device, and in response to the detection may reduce playback volume (of audio content of the speaker(s), TV etc.) The volume and TV etc. may then be turned off after 5-10 minutes when the device detects that the person has moved into a deeper sleep phase). Such detections may also serve as a control decision to dim lights automatically, set an automated burglar alarm, adjust heating/air-conditioning settings, activate a "do not disturb" function on an associated smart device(s) (e.g., smart phone), and so forth.

If sleep is detected by its processing, the smart speaker or processing device 100 may disable voice assistant prompts which can help to avoid accidentally waking a person. Such prompts may be disabled until a pre-defined wake-up window (e.g., permitting prompts such as to wake a person from a pre-selected stage of sleep so as to serve as a "smart alarm", and potentially minimize sleep inertia).

The processing device can make such control decisions dependent on a number of people detected in the sensing space. For example, if two persons are in a bed, and the device detects that one is asleep and the other is awake, the system can control a volume setting such as to reduce the voice assistant volume to the minimum possible while permitting it to still be used. This can allow the awake person to hear the device but it can also minimize the risk of the device waking the sleeping person. Conversely, if media content is playing (e.g., music, or a movie) when at least one awake person is detected and at least one sleeping person is detected, the device can refrain from lowering the media volume, or slightly reduce the media volume, for the person who is still awake. This device can then reduce further and turn off the medio content when the device detects that the remaining person(s) is/are also asleep.

In some cases, the processing device may control adjustments to the level of volume (audible audio content volume) based on the detection of location and/or presence of user(s) in a room of the processing device. For example, if no users are detected to be present, volume may be decreased or alternatively increased. The device may even control volume adjustments based on or as a function of detected location (e.g., distance from the processing device or particular place (e.g. bed) such as by increasing volume with increasing distance from the device and/or decreasing volume with decreasing distance from the device. By way of further example, if the processing device detects that that a user is in bed, volume may be decreased or if away from bed volume may be increased.

Wake Onset Services

The system can provide services for several waking scenarios. For example, if the user wakes during the night, they can receive voice assistance in order to help them fall back asleep—for example using a meditation program with personal feedback. Alternatively, or in addition to the voice assistance the system may control changes to other parameters and connected appliance settings to encourage the person to fall asleep again. This may include, for example, controlling a changing to a temperature setting, a lighting setting, a projection of images such as on a TV, display panel or produced by a projector, activating bed vibration such as with a connected/smart crib shaker etc. For example, in the case of a sleeping baby, once the acoustic motion sensing device detects that the baby may be about to wake up (e.g., by detecting a change from a deep sleep stage to a light sleep stage and an increase body movement) or that the baby is awake, a rocking cradle can be activated. Optionally, audio content may be played such as playing of children songs or music on the speaker of the smart device, or by playing some automated form of storytelling. This may help to prolong sleep time or the time during which the parents can delay attending to the baby, giving the parents of restless babies or toddlers badly needed brake.

If the user has set an alarm time window, the processing device can monitor the sleep stages of the user for a suitable sleep stage for waking the user up (usually—a light sleep stage). In the absence of such a stage, the processing device can also actively introduce subtle light and sounds to bring them from an alternate stage, such as a deep or REM sleep stage, to light sleep and then to wakefulness. Such a smart alarm processing device can also be configured to control additional connected home automation appliance functions. For example, upon detection of the waking user, the processing device may communicate with appliances such as automated curtains/blinds to open to promote wakefulness, an automated toaster oven to warm a breakfast, an automated coffee machine to turn on to begin making coffee etc.

A day nap program can also be configured using the biometric sensing. This can allow you to go have a nap, knowing you have an appointment at say 3.30 μm, and need to be awake and alert for this (i.e., not being woken directly from deep sleep, or indeed to prevent you entering deep sleep (so you don't feel groggy when woken) during the nap using light and sound stimulus.

Sleep Improvement Services

Advice can be delivered to the user to improve their sleep behavior (sleep hygiene) based on their recent trends, and population norms for persons of similar age, gender, lifestyle etc.

The described system further allows the collection of a feedback from the user. The feedback may be related to how the user currently feels, how the user slept last night, if the use of a provided advice, medicine or exercise was beneficial etc. Any such feedback can be collected by way of an input device. In one example, this could be the keyboard of a smartphone. Where the smart speaker includes a personal audio assistant application functionality, it is possible to elicit and process feedback from the user via voice—e.g., answering questions on their condition, asking how they feel, providing personalized feedback to them, including providing data on their sleepiness, and fatigue condition. Thus, the system, such as the processing device, may be configured with a software module for natural language processing to provide, as a conversational interface, directed conversational sequences (e.g., audible verbal commands/queries) with the system, such as to obtain information from the processing device that may be based on evaluation of the acoustically sensed motion signal. An example natural language processing module or conversational interface may be implemented with the Google Cloud platform, DialogFlow Enterprise development suite.

As an example, consider a multi-room or multi-floor property that has a set or plurality of processing devices 100. A processing device 100 with acoustic based sensing may be located in the kitchen and one may be located in a bedroom. While preparing breakfast, a person can query their sleep information by verbalizing: "OK google how was my sleep." In response the processing device can locate sleep parameters from a prior night's sleep session (and trends from prior nights) which may have been detected with the acoustic based motion sensing application of another processing device 100 (i.e., the one in the bedroom). Such queries to the processing device may be similarly applied to retrieving recorded session data from, for example, a Fitbit, Garmin watch, ResMed S+, and any other websites or networked servers that contain data relevant to the queried sleep etc.

Therefore, the person can choose when and in what form to receive advice about their sleep. In this regard, a sleep management system can deliver or present, interactively, sleep advice nuggets through audio content that is presented via a question and response verbal interrogation using the microphone(s) and speaker(s) of a processing device 100. The advice from a sleep management system, such as the sleep management system described in PCT/US2014/045814, may be delivered via the processing device 100, and could be related to changes in sleep habits, lifestyle changes, or indeed new product recommendations.

For example, an example query/answer interrogation session involving the speaker and microphone of the processing device 100 may generate the output of the following: "Hi Redmond, based on your recent sleep fragmentation, your purchase history, and your report of discomfort during the day, you may benefit from a new mattress. I have found a premium new inner-coil spring mattress on at a discounted special sale price, as you didn't like the memory foam option. Would you like to order it?". Such content may be collected and generated based on one or more searches of the internet and historic user data, as well as the detected sleep condition made by the processing device.

As such, the system allows the feedback and further operations based on, for example, acoustically made, sleep detections and interactive verbal communications (a conversation between the user and the voice assistant application of the processing device 100). Such feedback and operations may be based on the processing device accessing environment data (e.g., including sound data, temperature data, light data etc.) that it may search or otherwise detect with environmental related systems and sensors and may include generation of control signals to control the environmental systems' operations. The generated output of such a platform could also offer to sell relevant products for people such as to address sleep conditions. For example, the system may be developed on a platform using natural language to provide directed conversation with the system. Personalized sleep advice can then be presented in by interacting with the processing device 100 rather than mere transmission of sleep related messages. For example, a user may ask the processing device: "OK google how was my sleep last night?" "Oh hey Redmond this is the ResMed Sleep Score app, your score was 38 last night. Oh—that seems low." "What happened?" Well we spotted some issues with your sleep environment and your breathing patterns. Would you like to know more?" "Yes!" "Your bedroom was too warm at 77 deg F. We can activate your air-conditioning tonight an hour before bed—would you like to do this?" "Yes." "And tell me about my breathing." "We detected that you were snoring loudly last night, and had some gaps in your breathing during your dreaming REM sleep. Would you like to talk this through?" "Yes, tell me what this means." "Your snoring was severe last night, and there were some disruptions in your breathing pattern, and this is why your Score was low. Do you often feel tired during the day?" "Yes I do." "Would you like to open a call to a physician to discuss your symptoms? You can get a free 10 min consult on your health plan."

For such an interaction, the processing device 100, such as working in conjunction with processing of a support server on the network, can include an artificial intelligent (AI) process to provide improved flexibility and scope, such as by combining detected information (e.g., historic user data) from daytime activities (e.g., detected exercise or step information and heart rate such as from wearable GPS, accelerometers, heart rate sensors and other activity monitors that may also detect such information through motion sensing etc.) and detected sleep information in order to deliver tailored services, such as sleep related advice and product offers, based on the combined detected data.

Biometric Recognition Services (See Also Security Sensing)

The biometric features can be used for person recognition, and as outlined above the control of equipment in the living environment, and exchange of data with cloud services. For example, biometric recognition may be implemented by analysis of motion-related characteristics derived from the physiological motion signal(s). Such motion based biometric methods may be those described in PCT/EP2016/058789. Thus, biometric identification as described therein may be based on a motion signal that is derived from the acoustic-based sensing methodologies described herein.

Effecting person recognition using ultrasonic sensing implies that the processing device 100 distinguishes between background noise and the acoustic sensing signal, and is used in order to verify the presence of a person near the device. Thus, in some versions, the processing device 100 may be configured to operate a beam forming process, such as where suitable delay for different channels (different speaker signals) are learned so that the timing of acoustic signal reception may be adjusted for the differences associated with the detection vicinity and speaker location. As such, the system can use beam forming to further localize area detected (e.g., for detailed range detection, and object tracking). Such a process can run as a setup procedure or an adjustment procedure when a subject's presence is detected within the sensing vicinity.

As already noted, low frequency ultrasonics can yield a sophisticated security sensing platform such as when the processing device 100, detects absence/presence of subject in the detection range, and/or by then detecting and identifying a person based on biometric signal processing.

In some cases, the processing device 100 may even adapt its sensing signal to provide at least two modes. One mode may include a general monitoring mode aimed to detect when a person enters the monitored area, different detection schemes (e.g., UWB, CW, FMCW, etc.) may be employed for the presence detection. Once the presence of a person within the monitored are is detected, the system can switch to an enhanced ranging and optionally cardiac sensing, respiration sensing mode etc. (e.g., dual tone FMCW or (A)FHRG). The detected parameters (e.g., cardiac parameters, respiration parameters, gross body motion parameters, etc.) may then be used to identify the person, such as when the person's "signature" parameters are on accessible to the processing device (e.g., recorded data) or another device (e.g., a networked server) working in cooperation with the processing device. Alternatively, the processing device (or cooperating server) may decide that a new person has entered the sensing vicinity if such a signature is not recognized in relation to the recorded data.

Thus, the system, by sensing the area around the device, can detect an unknown or unrecognized biomotion signal or unrecognized gestures. Based on such a detection, the system, such as the processing device, may activate or communicate a warning or other message of potentially unwanted presence. One practical example includes a warning sent by a smartphone. The smartphone may determine that it has been forgotten/left unattended, when the phone detects, via the acoustic sensing and identification methods, that someone other than its recognized owner is using or attempting to use the phone.

In another example, a Google Home smart speaker, or other smart speaker or processing device, can monitor an apartment, room or house, using acoustic sensing, and can act as very intelligent intruder alarm. For example, the processing device may detect motion in the apartment, such as after a period of absence of motion. In response, the processing device may control one or more automated appliances. For example, secondary lights may be illuminated by a control signal generated or initiated by the processing device based on the detection. The processing may also initiate an interrogation via the speaker such as by audibly asking the person to identify himself or herself, or it may offer an audible welcome. The person may then say "It's Redmond". The processing device, via the microphone, may then evaluate the response such as by attempting to recognize its verbal signature in relation to a particular known person, for example, by comparing the audible response with previously recorded audible responses (e.g., sound wave analysis). If the speech is recognized, the processing device may end the challenge/response interrogation. If there is no response or if the processing device does not recognize the verbal signature, the processing device may communicate with other services such as via its communications interface. For example, it may, via a network or internet, inform another person or owner that there has been an intrusion (e.g., by controlling a generation of an email, text message, recorded audio message by phone etc.). In other words, the processing device, and optionally with one or more additional system processing devices or servers, has carried out: acoustically detect, audibly challenge, audibly authenticate, and authorize or communicate an alarm or warning message. Moreover, optionally, such as instead of, or in addition to the voice recognition, the processing device can perform a motion-based biometric authentication as previously discussed, such as by detecting breathing rate and heart rate, to provide a means of authentication or secondary authentication of the person in the vicinity of the processing device.

The processing device may be configured to conduct further processes, such as when the verbal signature of the person is recognized. For example, the processing device may then engage in further conversational interrogation, such as after turning on the lights. The processing device may ask the person about where he/she was previously. For example, before leaving the person (Redmond) may have told the processing device that he is going to the Gym or he engaged tracking services on his mobile phone or exercise device so that the tracked location (such as via GPS) was shared with the processing device. When the processing device detects a person's presence by acoustic detection (and optionally recognizes the user/Redmond), the processing device may initiate a conversation such as—"how did the gym go Redmond? Any personal bests?". The processing device may also detect arrival of a wireless device and initiate a download of data. For example, it might detect a wireless enabled movement/health tracker (e.g., a Bluetooth Fitbit) and it may download step counts, heart rate or other activity parameters. Such data may also serve to validate confidence of the authentication/recognition of the particular person. Additional conversation generated by the processing device may then be based on the downloaded data such as, for example, providing audible responses, via the speaker. Other parameters such as camera based facial or body recognition could also be initiated by the device, in a multi-modal identification, such as with a camera appliance that may be controlled by the processing device.

For a non-intruder alarm configuration, or when the person has already been identified, detected movement in a room can serve as a basis for control of a lighting change, for example, if dark is detected (which may be determined by time/clock or by a light sensor coupled to the processing device), the processing device can generate control signals to turn on, or otherwise increase illumination, with the lights via home automation or a light source in the processing device 100 itself.

A CW acoustic sensing mode can detect draughts (air currents) in a room—and could, for example, serve as a basis for generation of a reminder by the processing device, such as with an audible conversational message through the speaker, to a person that they may have left a window open, or that a fan may be operating etc. In some cases, an automated fan appliance may be activated or deactivated with a control signal of the processing device based on its detection of presence or absence of such draughts.

Range Detection

By detecting the distance of one or more persons from the speaker of the processing device 100, such as with the acoustic sensing methodologies described herein, different services can be delivered—either via audio through the speaker, or through other home automation services (e.g., appliance). For example, the processing device can set a volume level of the speaker(s) of the processing device, such as for the voice assistant application, to an appropriate level based on the detected distance from the speaker (e.g., louder for further away, lower for closer). Thus, the volume may be automatically changed based on detected user distance.

In some versions, other detections can also serve to improve distance detection. For example, range information may be derived from other sensors such as infrared components (e.g., IR proximity sensor). The distance detection can be combined to increase the accuracy of range (or indeed velocity) estimation.

Data from near and far field microphones can also be used to better localize the SONAR echoes—especially if both types of microphone are present on the same piece of hardware.

Gesture Control

The processing device may also be configured to recognize gestures based on the acoustic sensing methodologies described herein and by processing of the physiological motion signal. For example, the processing device may be configured to recognize characteristic gestures such as specific hand, arm, or leg movements from a motion signal as described in PCT/EP2016/058806, such as where the physiological motion signal is derived by the acoustic sensing methodologies herein. Thus, functions of the processing device, and/or functions of automated appliances that may be controlled by the processing device, can be adjusted according to detected gestures—e.g., a clockwise circular motion to increase volume on the speaker, and an anti-clockwise motion to reduce volume and optionally to turn off a device (e.g., the processing device 100 or any appliance described herein). A gesture may be used to control the processing device such as having it initiate a communication, such as sending a notification that may be made with the processing device such as a voice call or emergency call, text message, email, etc.

Breathing Control and Feedback Services

The processing device 100 can be implemented with daytime applications, such as for reducing stress and blood pressure, by generating meditation output, such as deep breathing exercises, based on the acoustically derived motion signal. For example, respiratory motion signals can be processed/evaluated by the processing device 100 to generate timing cues that can help to provide customized mindfulness breathing exercises (e.g., "belly breathing" at rates below 8 breaths per minute) by controller output via its speaker(s) and/or related appliances (e.g. controlled lights). The system can use entrainment of breathing to achieve a target value, such as where the device controls audible and/or visual feedback to the user, by relating the detected breathing curve to a breathing stimulus/cue delivered by the system.

The breathing cue could be an audible stimulus, where the system pre-filter music with a target breathing cadence, and then overlays with the sensing signal prior to playback. The system can also select a type of music with a tempo close to the user's detected breathing rate and/or heart rate.

A user's breathing pattern when anxious or stressed can be shallow and rapid, with the upper chest and neck muscles being used for breathing, instead of the abdominal muscles. Some advantages of personalized breathing coaching are for health improvement without drug intervention to potentially reduce stress hormones, "balance" the autonomic nervous system (parasympathetic and sympathetic), increase production of brain alpha waves, and improve the function of diaphragm and abdominal muscles (particularly in those with underlying respiratory conditions).

An exemplar relaxation game provided by the processing device may asks the user to breathe slowly and deeply, and based on a detection of the breathing motion by the processing device through is acoustic motion sensing, a shape may be presented on a display appliance that is controlled by the processing device. The ball or balloon may be controlled to inflate and deflate on the display in synchrony with the user's chest movement, as sensed automatically by the acoustic sensing method described herein. When the user reaches the target—such as three minutes of stable breathing with little movement, the processing device changes the display. For example, the balloon may float up to represent completion and the processing device may announce via the speaker that the user "wins". Where a cardiac signal is also detected by the processing device, increased coherence between breathing and heart rate can be used to gain extra points in the game. The shape can also be replaced by a light that changes intensity in synchrony with breathing, or a sound with a strong rhythmic component, and the reward for "winning" the relaxation game might be a change in light color, or a music sequence.

Other uses of the system are to provide alertness breathing exercises using one or more of paced illumination (via a light or display device) and/or specialized audio sequences to increase the user's breathing rate and modulate the user's inspiration/expiration time, optionally with biofeedback from the low frequency ultrasonic biometric detection.

Increase Privacy

Many virtual assistants are always listening (the microphone(s) remain(s) active) for speech recognition services (e.g., listening continuously locally for keywords/phrases etc. "OK Google", "Alexa", "Hey Siri"). In this regard, they are normally active. Anything said after the keyword/key phrase may be sent to the internet. Some people are not comfortable with the fact that their conversations are constantly monitored in this fashion. One advantage of the above described movement detection is that it allows the processing device to deactivate its microphone until the user is ready to use the processing device. In this regard, the voice assist operation of the processing device may configured to be normally inactive. For example, the processing device may apply its acoustic motion detection methodologies, such as by detecting a particular motion or motion gesture, to initiate microphone monitoring rather than using the typical audio keyword recognition with the microphone. This removes the need for constant monitoring of the user's conversation and allows the user more privacy. While such a motion detection may be made closely proximate to the processing device, it may also be detected in the vicinity surrounding the processing device. Such a method may use a standard motion gesture or user customized motion gesture (e.g., learned in a setup process) to trigger the processing device to activate the speaker. This may initiate a natural language session with the processing device such as triggering a verbal response from the processing device via the speaker. However, optionally, the processing device may additional wait to detect an audible keyword with the microphone following its activation. The verbal keyword may then serve as the trigger for initiating a natural language conversation session with the processing device 100.

Such a methodology for waking up processing device or initiating a session may be more preferable to conventional methods. For a user who is still and talking, the assistant application of the processing device would not listen for verbal keyword, until motion is detected. Such a feature may also mean that the processing device is not listening for speech (or other noises in the room) while there is nobody in the room. However, such active listening mode may be selectively turned on to a more continuous basis such as if the user is leaving ("Please monitor the room because I am leaving now").

Another privacy advantage is that detailed sleep tracking or daytime absence/presence, respiration and/or heart rate tracking is possible without requiring recording cameras in the bedroom/living room.

Other Applications

Other uses of the technology include cases where speakers and microphones are already available, or could be easily retrofitted. For example, for occupancy sensor in lifts (elevators and the existing speaker and microphone (used for emergency communication) could be used to sense breathing or other movement signal(s) in the space.

It is also possible to use public address (PA) systems for sensing across range using FMCW, or large area sensing using CW. Many such systems already use 20 kHz or similar tones to ensure they are functioning correctly, and could be upgraded to include ultrasonic biometric sensing (e.g., for use in railway stations, libraries, shops etc.).

Power Nap

The processing device 100 of the system can be programmed with a nap function to assist with a smart nap, whether the person is lying in bed, on a couch, or in any area/vicinity of the processing device. For example, the user can tell the device "I am taking a nap." The interactive audio device can then audibly help the user fall asleep and then, by monitoring sleep and/or time, guide a person to an appropriate duration of nap based on the expected available time, an estimate of current sleep deficit, time of day, and user request. For example, it may optimize to target durations such as a 20 min, 30 min, 60 min or 90 min (full sleep cycle). The 60 min nap is to optimize deep sleep and allowing some time to recover at the end from any sleep inertia, whereas the 20 and 30 min target times are optimized to wake the user while they are still in light sleep, or before being in deep sleep for more than a minute or two. The time awake before sleep (nap) is also recorded in addition to the nap time.

A 20-25 min nap can be preferential to a 90 min full sleep cycle if the user is sleeping normally in the preceding days, as the longer period can impact sleep that night.

Multi-User Vicinity Sensing

In some versions, the processing device may be configured to monitor two people (or more) at the same time with a one or more speaker(s) and one or more microphone(s). For example, a processing device may produce multiple sensing signals at different sensing frequencies for sensing different users with different frequencies. In some cases, it may control producing interleaved sensing signals (e.g., different sensing signals at different times) for sensing different users at different times. In some cases, it may adjust sequentially adjust range gating for sensing different ranges at different times (e.g., for in parallel sensing).

In some cases, there are some conditions that can help to maximize signal quality. For example, a processing device (e.g., either an RF sensor, or a SONAR enabled smartphone) may be placed on a bedside locker. In this case, there might be a "shadowing" effect of the first person whose body can block quite a lot of the sensing signal (and actually benefits range gating (sensing just one person in bed). In SONAR, the processing device can generate two (or more) different sensing signals—or even a single FMCW (triangle, dual ramp or other) sensing signal to detect two (or more) people. The range separability of FMCW means that one sensing signal is sufficient (such as if there is only one speaker/mic in the room). Ideally, to monitor two people at the same time, a user may places the processing device in an elevated position so that the majority of the acoustic energy reaches both users (for example so that the first user and his/her sheet/duvet comforter does not block too much of the sensing signal). If there are two microphones on the same device, this can also provide an advantage if there is significant constructive/destructive interference (e.g., as it may be closer to a peak on one, and a null on the other—especially for the smaller amplitude receive signals from the more distant subject).

It may be more beneficial (and potentially achieve a higher signal quality), if there is a SONAR/smartphone closer to the second person. The second person may use their smartphone/processing device and the first person uses their smartphone/processing device. The sensing signals can be generated to avoid interference with each other (i.e., keep from overlapping in time and/or frequency). The devices may automatically sense the environment (either by listening before transmitting and/or processing the received signal when we are transmitting) so as to selective choose a sensing signal modulation/technique that does not interfere with pre-existing sensing signals from other devices in the vicinity.

In some cases, the sound pressure level of the transmit and the receive sensitivity are such that two smartphones with exactly the same transmit sensing signal will not cause interference, as the mixture of air attenuation, and acoustic absorptive surfaces (fabrics, carpets, bed clothing etc.) can have an impact that keeps the second source below an interference threshold. If each processing device used by a respective user, the devices can be configured to optionally automatically decrease the output power of each so that biometrics signals of the monitored subject may be sufficiently detected such as with the lowest necessary output power. Such processes can permit each to detect motion while avoiding interference with other devices.

Noise/Interference Avoidance

In some cases, when a processing device plays a content sound (e.g., music, speech etc.) on a speaker, the processing device may low pass this content sound to remove any content over (for example) 18 kHz. The processing device may then overlay the low frequency ultrasonic signal for sensing. This means the system removes (or significantly attenuates) components of the "music" that might impinge the sensing abilities. However, in some cases such filtering may be omitted. Such filtering can muddy the content sound (impact the highs) on high quality Hi-Fi's (or it might cause the user to think that this might happen—a perception rather than reality issue). The processing device might be configured to refrain from low pass filtering the music/sound content (or indeed might not even have the ability to filter it, if played on a separate but nearby speaker). Thus, there may be unwanted components in the sensing signal. One way to mitigate this is to implement feedback on realtime and recent (in time) "in-band" interference to adapt the sensing signal. Depending on processing resources that may be insufficient (or want to act very fast (low latency)), the processing device may transmit two sensing signals at the same time (in the case of an FMCW signals—which could be two co-located triangular ramps or indeed two sets of dual ramps etc.). The processing device may then include a voting process to evaluate the resulting biomotion signals to select the better signal (in terms of signal quality) based on the detected motion in the signals. Such a process may continue dynamically throughout sensing processing (time of use).

5.2 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the present technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilized to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

The invention claimed is:

1. A non-transitory processor-readable medium, having stored thereon processor-executable instructions which, when executed by a processor of an interactive audio device, cause the processor to detect physiological movement of a user, the processor-executable instructions comprising:
   instructions to control transmitting, via a transmitter that is coupled to the interactive audio device, a radio frequency (RF) signal in a vicinity of the interactive audio device;
   instructions to control sensing, via a receiver that is coupled to the interactive audio device, a reflection of the transmitted signal;
   instructions to derive a physiological movement signal with at least a portion of the sensed reflected signal and a signal representative of at least a portion of the transmitted signal;
   instructions to generate a control signal to control a change in operation of the interactive audio device comprising activating microphone sensing for initiating interactive voice assistant operations of the interactive audio device, whereby an inactive interactive voice assistant process is engaged, wherein initiating the interactive voice assistant operations is further based on detection of a verbal keyword by the microphone sensing; and
   instructions to generate an output based on an evaluation of at least a portion of the derived physiological movement signal, and
   wherein the generated output comprises an interactive query and response presentation.

2. The non-transitory processor-readable medium of claim 1, wherein the derived physiological movement signal comprises one or more of respiratory motion, gross motion, or cardiac motion.

3. The non-transitory processor-readable medium of claim 1, further comprising the processor-executable instructions to evaluate, via a microphone coupled to the interactive audio device, a sensed audible verbal communication; and wherein the instructions to generate the output are configured to generate the output in response to the sensed audible verbal communication.

4. The non-transitory processor-readable medium of claim 1, further comprising processor-executable instructions to operate a beam forming process to further localize a detected area.

5. The non-transitory processor-readable medium of claim 1, wherein the generated output based on the evaluation of the portion of the derived physiological movement signal comprises monitored user sleep information.

6. The non-transitory processor-readable medium of claim 1, wherein the evaluation of the portion of the derived physiological movement signal comprises detecting one or more physiological parameters, comprising any one or more of breathing rate, relative amplitude of breathing, heart rate, cardiac amplitude, relative cardiac amplitude, and heart rate variability.

7. The non-transitory processor-readable medium of claim 1, wherein:
   (a) the generated output comprises an interactive query and response presentation effected by way of a speaker; or
   (b) the generated output comprises an interactive query and response presentation effected by way of a speaker and comprises advice to improve user sleep.

8. The non-transitory processor-readable medium of claim 1, wherein:
(a) the generated output based on the evaluation of the portion of the derived physiological movement signal is further based on accessing a server on a network and/or conducting a search of a network resource;
(b) the generated output based on the evaluation of the portion of the derived physiological movement signal comprises a control signal to control an automated appliance or a system; or
(c) the generated output based on the evaluation of the portion of the derived physiological movement signal comprises a control signal to control an automated appliance or a system and the processor-readable medium further comprises processor control instructions to transmit the control signal to the automated appliance or system over a network.

9. The non-transitory processor-readable medium of claim 1, further comprising:
(a) processor control instructions to generate a control signal to change a setting of the interactive audio device based on an evaluation of at least a portion of the derived physiological movement signal; or
(b) processor control instructions to generate a control signal to change a setting of the interactive audio device based on an evaluation of at least a portion of the derived physiological movement signal, wherein the control signal to change a setting of the interactive audio device comprises a change in volume based on a detection of user distance from the interactive audio device, user's state or user's location.

10. The non-transitory processor-readable medium of claim 1, wherein the processor-executable instructions are configured to evaluate motion characteristics of different sensing ranges to monitor sleep characteristics of a plurality of users.

11. The non-transitory processor-readable medium of claim 1, further comprising processor-executable instructions to detect presence or absence of a user based on at least a portion of the derived physiological movement signal.

12. The non-transitory processor-readable medium of claim 1, further comprising processor-executable instructions to conduct biometric recognition of a user based on at least a portion of the derived physiological movement signal.

13. The non-transitory processor-readable medium of claim 1, further comprising processor-executable instructions to generate a communication over a network based on (a) a biometric evaluation determined from an analysis of the derived physiological movement signal, and/or (b) a detected presence determined from an analysis of at least a portion of the derived physiological movement signal.

14. The non-transitory processor-readable medium of claim 1, further comprising processor-executable instructions configured to cause the interactive audio device to detect motion presence of a user, audibly challenge the user, audibly authenticate the user, and authorize the user or communicate an alarm message about the user.

15. The non-transitory processor-readable medium of claim 14, wherein:
(a) the processor-executable instructions to audibly authenticate the user are configured to compare a verbal sound wave of the user, sensed by a microphone that is coupled to the processor, with a previously recorded verbal sound wave; and/or
(b) processor-executable instructions are configured to authenticate the user with motion-based biometric sensing.

16. The non-transitory processor-readable medium of claim 1, further comprising:
processor-executable instructions to cause the interactive audio device to detect a motion gesture based on at least a portion of the derived physiological movement signal; and
processor-executable instructions to generate the control signal, based on the detected motion gesture.

17. The non-transitory processor-readable medium of claim 16, further comprising processor-executable instructions to generate a control signal, based on the detected motion gesture, to send a notification, or to control a change to an operation of an automated appliance.

18. The non-transitory processor-readable medium of claim 1, further comprising:
processor-executable instructions to cause the interactive audio device to receive a communication from another interactive audio device, controlled by another processing device via inaudible sound waves sensed by a microphone of the interactive audio device.

19. The non-transitory processor-readable medium of claim 1, wherein:
(a) the evaluation of the portion of the derived physiological movement signal further comprises a detection of sleep onset or wake onset, and wherein the output based on the evaluation comprises a service control signal; or
(b) the evaluation of the portion of the derived physiological movement signal further comprises a detection of sleep onset or wake onset, and wherein the output based on the evaluation comprises a service control signal, and wherein the service control signal comprises one or more of: a lighting control; an appliance control; a volume control; a thermostat control; and a window covering control.

20. The non-transitory processor-readable medium of claim 1, further comprising processor-executable instructions to provide a sleep improvement service, the sleep improvement service comprising any of: (a) generating advice in response to detected sleep condition and/or collected user feedback; and (b) generating control signals to control environmental appliances to set environmental sleep conditions and/or provide a sleep related advice message to the user.

21. The non-transitory processor-readable medium of claim 1, further comprising processor-executable instructions to detect a gesture based on at least a portion of the derived physiological movement signal and to initiate microphone sensing for initiating interactive voice assistant operations of the interactive audio device.

22. The non-transitory processor-readable medium of claim 1, further comprising processor-executable instructions to initiate and monitor a nap session based on at least a portion of the derived physiological movement signal.

23. The non-transitory processor-readable medium of claim 1, further comprising processor-executable instructions to vary a detection range by varying parameters of at least a portion of the transmitted signal to track movement of a user through the vicinity.

24. The non-transitory processor-readable medium of claim 1, further comprising:
(a) processor-executable instructions to detect unauthorized movement with at least a portion of the derived physiological movement signal and generate an alarm or a communication to notify the user or a third party; or (b) processor-executable instructions to detect unauthorized movement with at least a portion of the derived physiological movement signal and generate an alarm or a communication to notify the user or a third party, wherein the communication provides an alarm on a smart phone or smart watch.

25. A server with access to the non-transitory processor-readable medium of claim 1, wherein the server is configured to receive requests for downloading the processor-executable instructions of the processor-readable medium to an interactive audio device over a network.

26. An interactive audio device comprising: one or more processors; a speaker coupled to the one or more processors; a microphone coupled to the one or more processors; and the non-transitory processor-readable medium of claim 1.

27. The interactive audio device of claim 26, wherein the interactive audio device comprises a mobile phone, a smart watch, a tablet computer or a smart speaker.

28. A method of a server having access to the non-transitory processor-readable medium of claim 1, the method comprising receiving, at the server, a request for downloading the processor-executable instructions of the processor-readable medium to an interactive audio device over a network; and transmitting the processor-executable instructions to the interactive audio device in response to the request.

29. A method of an interactive audio device to detect physiological movement of a user, the method comprising:
   transmitting, from the interactive audio device, a signal in a vicinity of the interactive audio device;
   sensing, by the interactive audio device, a reflection of the transmitted signal;
   deriving, in a processor, a physiological movement signal with at least a portion of the sensed reflected signal and a signal representative of at least a portion of the transmitted signal;
   generating a control signal to control a change in operation of the interactive audio device comprising activating microphone sensing for initiating interactive voice assistant operations of the interactive audio device, whereby an inactive interactive voice assistant process is engaged, wherein initiating the interactive voice assistant operations is further based on detection of a verbal keyword by the microphone sensing; and
   generating from the processor an output based on an evaluation of at least a portion of the derived physiological movement signal, and
wherein the generated output comprises an interactive query and response presentation.

30. A non-transitory processor-readable medium, having stored thereon processor-executable instructions which, when executed by a processor of an interactive audio device, cause the processor to detect physiological movement of a user, the processor-executable instructions comprising:
   instructions to control transmitting, via a transmitter that is coupled to the interactive audio device, a radio frequency (RF) signal in a vicinity of the interactive audio device;
   instructions to control sensing, via a receiver that is coupled to the interactive audio device, a reflection of the transmitted signal;
   instructions to derive a physiological movement signal with at least a portion of the sensed reflected signal and a signal representative of at least a portion of the transmitted signal;
   instructions to generate a control signal to change a setting based on an evaluation of at least a portion of the derived physiological movement signal, wherein the control signal to change a setting comprises a change in volume of the interactive audio device, a change to a temperature setting, a change to a lighting setting, a change to a projection of images, or a change to a bed parameter, based on a detection of user distance from the interactive audio device, user's state or user's location; and
   instructions to generate an output based on an evaluation of at least a portion of the derived physiological movement signal, and
   wherein the generated output comprises an interactive query and response presentation.

31. A method of an interactive audio device to detect physiological movement of a user, the method comprising:
   transmitting, from the interactive audio device, a signal in a vicinity of the interactive audio device;
   sensing, by the interactive audio device, a reflection of the transmitted signal;
   deriving, in a processor, a physiological movement signal with at least a portion of the sensed reflected signal and a signal representative of at least a portion of the transmitted signal;
   generating a control signal to change a setting based on an evaluation of at least a portion of the derived physiological movement signal, wherein the control signal to change a setting comprises a change in volume of the interactive audio device, a change to a temperature setting, a change to a lighting setting, a change to a projection of images, or a change to a bed parameter, based on a detection of user distance from the interactive audio device, user's state or user's location, and
   generating from the processor an output based on an evaluation of at least a portion of the derived physiological movement signal, and
wherein the generated output comprises an interactive query and response presentation.

* * * * *